(12) United States Patent
Bosch i Lladó et al.

(10) Patent No.: US 8,580,972 B2
(45) Date of Patent: Nov. 12, 2013

(54) PROCESSES FOR THE PREPARATION OF 5-CHLORO-2-METHYL-2,3,3A,12B-TETRAHYDRO-1H-DIBENZO[2,3:6,7]OXEPINO[4,5-C]PYRROLE

(75) Inventors: Jordi Bosch i Lladó, Girona (ES); Ernesto Duran Lopez, Castellbisbal (ES)

(73) Assignee: Medichem, S.A., Barcelona (ES)

( * ) Notice: Subject to any disclaimer, the term of this patent is extended or adjusted under 35 U.S.C. 154(b) by 0 days.

(21) Appl. No.: 13/336,201

(22) Filed: Dec. 23, 2011

(65) Prior Publication Data

US 2012/0165545 A1 Jun. 28, 2012

(30) Foreign Application Priority Data

Dec. 24, 2010 (EP) .................................. 10382354

(51) Int. Cl.
*C07D 491/22* (2006.01)
(52) U.S. Cl.
USPC ....................................................... 548/421
(58) Field of Classification Search
USPC ....................................................... 548/421
See application file for complete search history.

(56) References Cited

U.S. PATENT DOCUMENTS

| 4,145,434 A | 3/1979 | van der Burg |
| 7,964,739 B2 | 6/2011 | Kemperman |
| 2011/0046393 A1 | 2/2011 | Wang et al. |

FOREIGN PATENT DOCUMENTS

| EP | 1 710 241 A1 | 10/2006 |
| EP | 2 166 012 A1 | 3/2010 |
| JP | 49-69697 | 7/1974 |
| WO | WO 2009/087058 A1 | 7/2009 |

OTHER PUBLICATIONS

Grant & Hackh's Chemical Dictionary (5th Ed. 1987) at p. 148.*
Vader et al., "The syntheses of radiolabelled org 5222 and its main metabolite org 30526," *Journal of Labelled Compounds and Radiopharmaceuticals* (1994) 34 (9): 845-869.
van der Linden et al., "Debottlenecking the synthesis route of Asenapine," *Organic Process Research & Development* (2008) 12: 196-201.
Constable et al. "Key green chemistry research areas—a perspective from pharmaceutical manufacturers." *J. of Royal Soc. of Chem. Green Chem.* vol. 9. 2007. pp. 411-420.
Fernandes et al. "Reduction of amides with silanes catalyzed by $MoO_2Cl_2$" *J. of Molecular Catalysis A: Chem.* vol. 272. 2007. pp. 60-63.
Communication from EPO for application No. 11195387.3 mailed Sep. 17, 2013 (10 pages).

\* cited by examiner

*Primary Examiner* — Samantha Shterengarts
(74) *Attorney, Agent, or Firm* — Merchant & Gould P.C.

(57) ABSTRACT

This invention provides improved processes for the preparation of 5-chloro-2-methyl-2,3,3a 12b-tetrahydro-1H-dibenzo[2,3:6,7]oxepino[4,5-c]pyrrole, asenapine. These processes allow the preparation of asenapine at industrial scale in good yields and high stereoselectivity.

14 Claims, No Drawings

PROCESSES FOR THE PREPARATION OF 5-CHLORO-2-METHYL-2,3,3A,12B-TETRAHYDRO-1H-DIBENZO[2,3:6,7]OXEPINO[4,5-C]PYRROLE

PRIORITY CLAIM

Priority under §119 is made to European Patent Application 10382354.8, filed Dec. 24, 2010, the contents of which are incorporated by reference.

TECHNICAL FIELD

This invention relates to improved processes for the preparation of 5-chloro-2-methyl-2,3,3a,12b-tetrahydro-1H-dibenzo[2,3:6,7]oxepino[4,5-c]pyrrole.

BACKGROUND

Asenapine (compound trans-(I)) is the international commonly accepted non-proprietary name for trans-5-chloro-2-methyl-2,3,3a,12b-tetrahydro-1H-dibenzo[2,3:6,7]oxepino[4,5-c]pyrrole, and has an empirical formula of $C_{17}H_{16}NOCl$ and a molecular weight of 285.77. The molecule has two chiral centers but has been developed as the racemic mixture of the trans isomer.

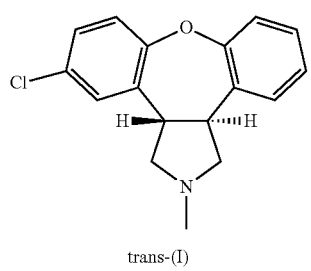 [SMILES: CN1C[C@@H]2c3ccccc3Oc3ccc(Cl)cc3[C@H]2C1]

trans-(I)

The maleic acid salt (1:1) of asenapine is known to be therapeutically useful and is commercially marketed for the treatment of schizophrenia and acute manic or mixed episodes associated with bipolar 1 disorder. Asenapine maleate exhibits high affinity and potency for blocking dopamine, serotonin, α-adrenergic and histamine receptors, and no appreciable activity at muscarinic and cholinergic receptors. The rank order of receptor affinity for asenapine maleate reveals a unique human receptor binding signature, characterized by strong serotonergic properties, when compared to other antipsychotic drugs. In the United Stated, asenapine maleate is marketed under the name Saphris™. In Europe, asenapine maleate is marketed under the name Sycrest™.

Asenapine was first described in Example IV of U.S. Pat. No. 4,145,434 ("the '434 patent"). The synthetic process was summarized in a flow sheet in the '434 patent (see Scheme 1), while experimental steps were first described in *J. Labelled Compd. Radiopharm.* 1994, 34, 845-869.

Scheme 1

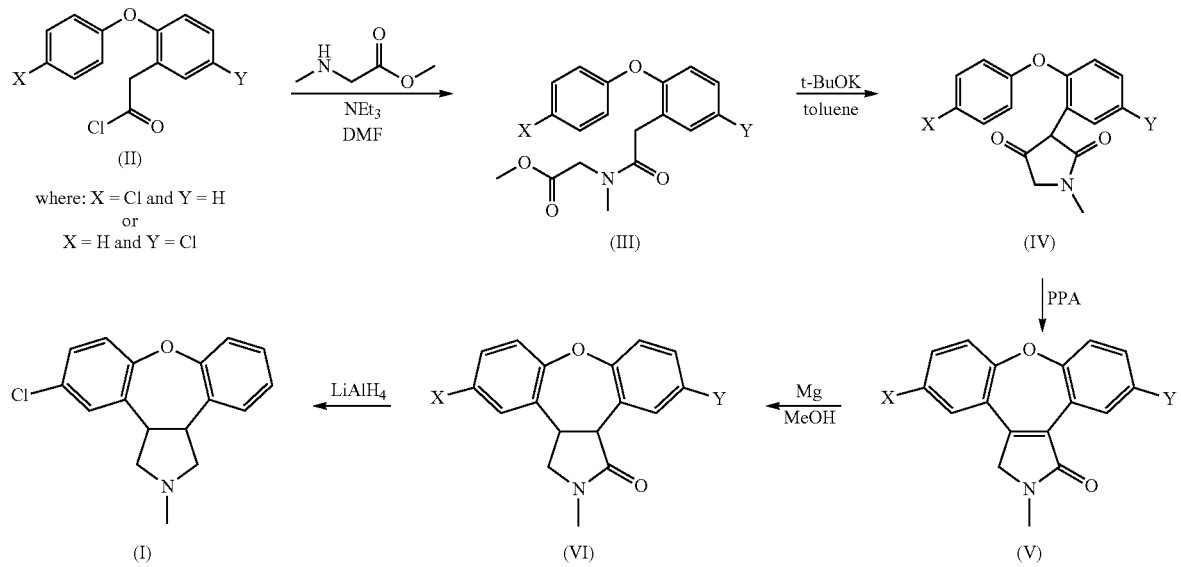

The reduction of enamide (V) as disclosed in the '434 patent is described to be a major bottleneck for the scale-up of the process to commercial production (see *Org. Process Res. Dev.* 2008, 12, 196-201). This step is carried out by a magnesium/methanol reduction of the carbon-carbon double bound, which gives rise to the formation of the desired trans-lactam trans-(VI) and its undesired cis-isomer cis-(VI) in an unfavorable ratio of approximately 1:4, together with a significant amount of side products (see Scheme 2). During this process, large amounts of extremely flammable hydrogen gas are formed because of the inevitable highly exothermic side reaction of magnesium with methanol. Additionally, there is no control over the rate in which the heterogeneous reaction between magnesium and methanol takes place. Because of the potential danger of the accumulated heat, a calorimetric study of the original process determined the maximum reaction scale to be only about 10-15 Kg (see *Org. Process Res. Dev.* 2008, 12, 196-201).

Scheme 2

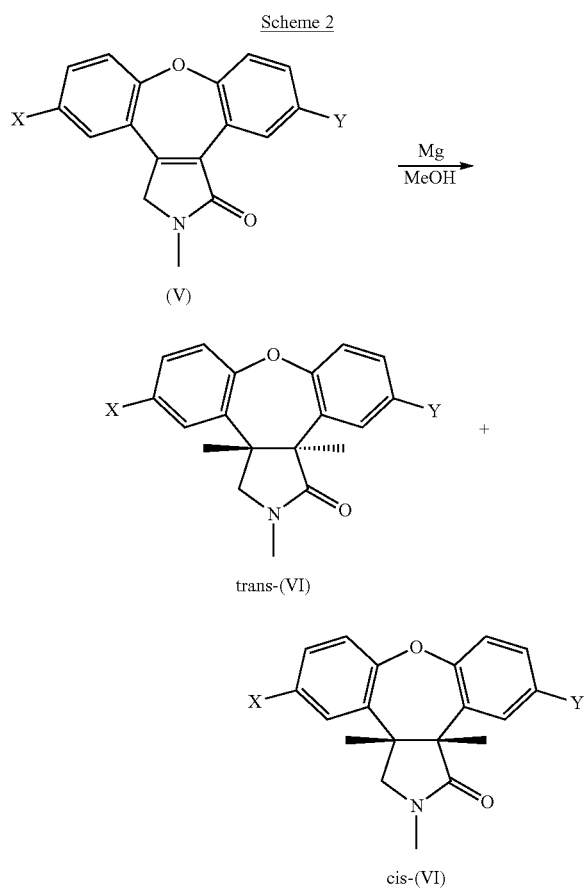

where: X = Cl and Y = H
or
X = H and Y = Cl

Despite of the drawbacks of the original process, Org. Process Res. Dev. 2008, 12, 196-201 describes that all attempts to develop an alternative process for the magnesium/methanol reduction were unsuccessful (e.g. catalytic hydrogenation in the presence of a variety of palladium, platinum, rhodium, ruthenium and iridium catalysts, different ligands and solvents at pressures varying between 1 and 5 bar; use of zinc powder; Birch reduction using lithium in ammonia; use of magnesium in combination with less acidic alcohols like ethanol or propanol). Org. Process Res. Dev. 2008, 12, 196-201 discloses the dosing of magnesium in portions over a solution of enamide (V) as a way to transform the original process into a safer and more efficient process, since only magnesium in combination with methanol was found to be able to reduce the double bound of enamide (V). However, this process requires the use of some equipments that are not conventional at industrial scale, like solid-addition funnels. Another drawback is that, despite of carrying out the addition of magnesium in portions, a very high amount of heat is released after each addition due to the exothermic reaction between magnesium and methanol (see FIG. 2 in Org. Process Res. Dev. 2008, 12, 196-201). Furthermore, despite of the portion-wise addition of magnesium, about two molar equivalents of hydrogen are still released in an uncontrolled manner due to the side reaction between magnesium and methanol. These drawbacks make this reduction process non viable for an industrial production of asenapine due to safety reasons.

European Patent EP 1710241 B1 describes that some of the disadvantages of the process described in the '434 patent, specially the unfavourable trans-(VI)/cis-(VI) product ratio, can be improved by subsequent partial isomerization of the unwanted cis-isomer cis-(VI) into the trans-isomer trans-(VI) using 1,5-diazabicyclo[4.3.0]non-5-ene (DBN), leading to a thermodynamic equilibrium ratio of trans-isomer trans-(VI) to cis-isomer cis-(VI) of 1:2. Isomers can be separated by chromatography over silica gel, and the cis-isomer cis-(VI) can be isomerized again using DBN resulting in a 1:2 mixture of trans-(VI) and cis-(VI), from which the trans-(VI) can be again separated by chromatography. However, after further repetition of this cycle at kg scale, recrystallization of the three combined fractions of the trans-isomer trans-(VI) produced trans-(VI) in an overall yield of only 38% starting from the enamide (V). Moreover this process involves chromatography, normally not easily implemented at industrial scale.

EP 1710241 B1 also describes a process, again based on the reduction of compound (V) with Mg/MeOH, in which the mixture of cis- and trans-lactams cis-(VI) and trans-(VI), can be treated in an alcoholic solution comprising an excess of strong alkaline base thereby producing a mixture of amino acids trans-(VII) and cis-(VII). The ring-opening reaction is described to be stereoselective, resulting in a 10:1 ratio of the trans-isomer trans-(VII) to the cis-isomer cis-(VII). The trans-amino acid derivative trans-(VII) can be isolated and cyclized to give trans-(VI), with preservation of the trans-stereochemistry, but with an overall yield of only 62% from the enamide (V) (see Scheme 3).

Scheme 3

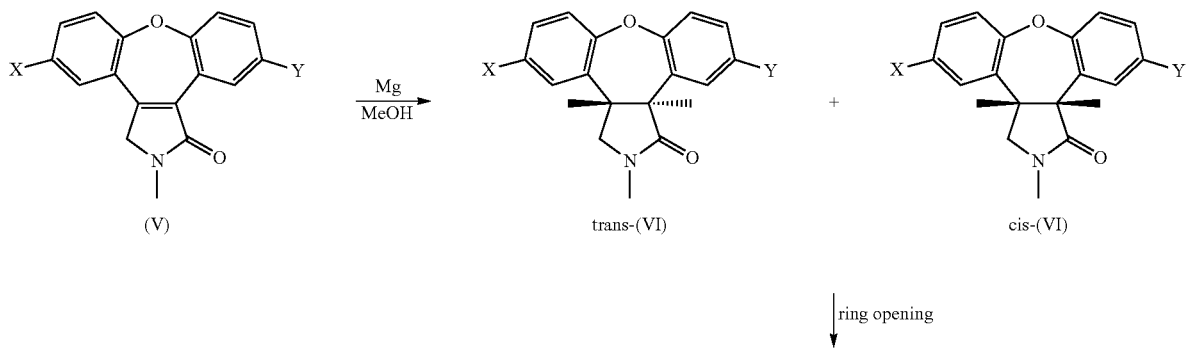

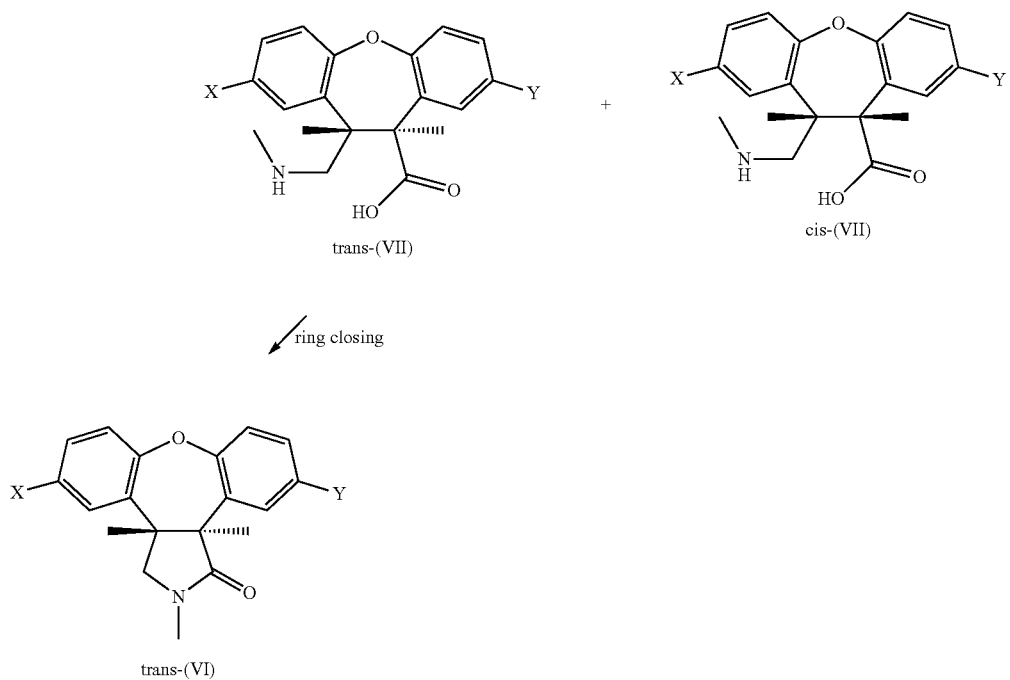

where: X = Cl and Y = H
or
X = H and Y = Cl

Example 8 of the European Patent EP 1710241 B1 also describes an alternative process for the synthesis of the lactam (VI), see Scheme 4. In this example, (5-chloro-2-phenoxyphenyl)acetic acid methyl ester (compound VIIIa) is reacted with methyl formate in the presence of potassium tert-butoxide to give 2-(5-chloro-2-phenoxyphenyl)-3-hydroxyacrylic acid methyl ester (compound IXa, E/Z mixture 9:1), which is directly cyclized with pyrophosphoric acid to obtain methyl 2-chlorodibenzo[b,f]oxepin-11-carboxylate (compound Xa), referred to us 8-chlorodibenzo[b,f]oxepin-10-carboxylic acid methyl ester in EP 1710241 B1, with 85% yield. This compound is then reacted with nitromethane in the presence of tert-butyl-tetramethylguanidine to give methyl 2-chloro-10-nitromethyl-10,11-dihydrodibenzo[b,f]oxepine-11-carboxylate (compound XIa), referred to us 8-chloro-1'-nitromethyl-10,11-dihydrodibenzo[b,f]oxepine-10-carboxylic acid methyl ester in EP 1710241 B1, with a trans to cis ratio of 8:1, which is directly hydrogenated in the presence of a sponge nickel catalyst to give methyl 10-aminomethyl-2-chloro-10,11-dihydrodibenzo[b,f]oxepine-11-carboxylate (compound XIIa), referred to us 11-aminomethyl-8-chloro-10,11-dihydrodibenzo[b,f]oxepine-10-carboxylic acid methyl ester in EP 1710241 B1, which after treatment with potassium tert-butoxide and dimethyl sulphate, is converted into the lactam (VIa) with an overall yield of 81% from compound (Xa), but predominantly corresponding to the undesired cis-isomer (approximately 85:15 ratio with respect to the trans-isomer), being therefore necessary to carry out one of the above described low-yield processes for the conversion of undesired cis-(VI) to trans-(VI).

Scheme 4

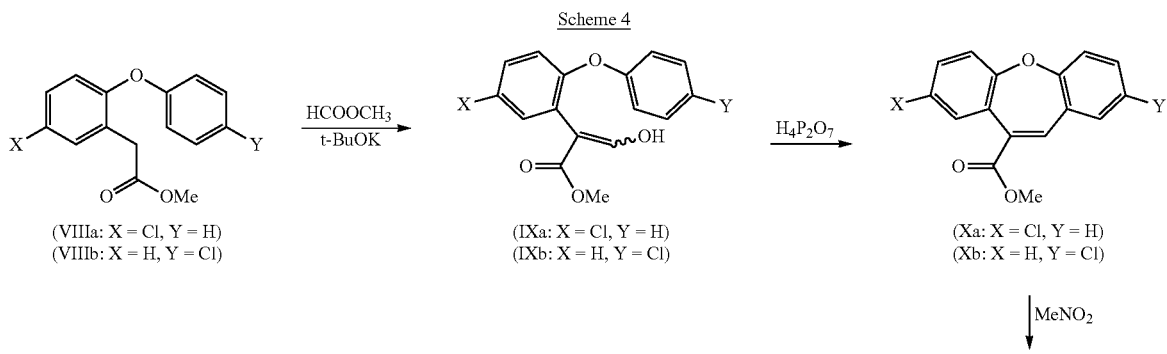

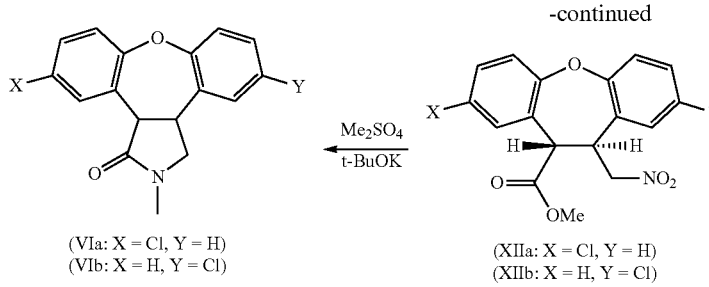

(VIa: X = Cl, Y = H)
(VIb: X = H, Y = Cl)

←—— Me₂SO₄ / t-BuOK ——

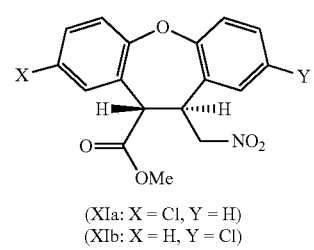

(XIIa: X = Cl, Y = H)
(XIIb: X = H, Y = Cl)

←—— H₂ / sponge Nickel catalyst ——

(XIa: X = Cl, Y = H)
(XIb: X = H, Y = Cl)

DISCLOSURE OF THE INVENTION

It is an object of the present invention to provide simple processes for preparing asenapine at industrial scale which overcome the drawbacks disclosed in the prior art. Additional advantages of the processes as herein disclosed is that asenapine is obtained in high yield and stereoselectivity.

In a first aspect of the present invention, compound trans-(I) or a salt thereof can be obtained in good yields with reduced formation of undesired cis isomers by a process comprising:

(a) reducing desmethyl-lactam (XVII),

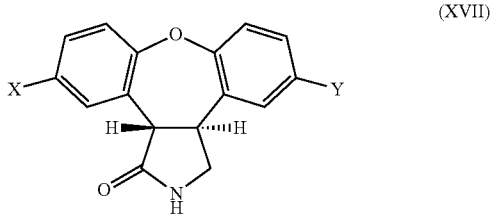

(XVII)

to give desmethylasenapine (XVIII),

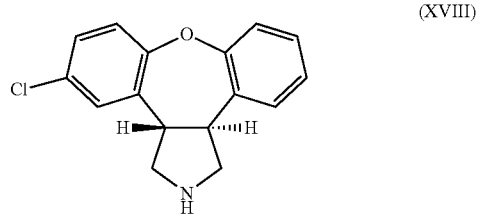 [SMILES: Clc1ccc2c(c1)[C@H]1CNC[C@@H]1c1ccccc1O2]

(XVIII)

(b) methylating desmethylasenapine (XVIII) to give compound trans-(I); and
(c) optionally converting compound trans-(I) to a salt thereof, wherein X is H and Y is Cl or wherein X is Cl and Y is H.

This process allows the conversion of desmethyl-lactam (XVII) into asenapine trans-(I) avoiding any step, such as the conversion of trans-(XII) to lactam trans-(VI) described in EP 1710241 B1, which can favour the isomerization of the trans compounds into the cis compounds.

Reduction of desmethyl-lactam (XVII) into desmethylasenapine (XVIII) can be carried out by using reducing agents. As used herein, the term "reducing agent" refers to reagents used for the reduction of an amide functionality to the corresponding amine. Examples of reducing agents and methods include, but are not limited to: silanes such as triethylsilane, diphenylsilane or trichlorosilane, optionally in the presence of one or more Lewis acids, such as trifluoroborane, titanium chloride, aluminium chloride, zinc iodide or trifluoroacetic acid, also in form of complexes with ethers, such as boron trifluoride diethyl etherate; borohydrides such as sodium borohydride, potassium borohydride, lithium borohydride, sodium cyanoborohydride, potassium cyanoborohydride, lithium cyanoborohydride or mixtures thereof, also in the presence of suitable additives such as sulfuric acid, methanesulfonic acid, acetic acid, titanium chloride, cobalt (II) chloride, aluminium chloride, tin chloride, phosphorus oxychloride, methanesulfonic anhydride, trifluoromethanesulfonic anhydride, pyridine, trifluoroethanol or 1,2-ethanedithiol; boranes such as borane, diborane or catechol borane, also in the form of complexes with ethers, sulfides or amines such as $BH_3.SMe_2$, $BH_3.Et_2O$, $BH_3.THF$ or $BH_3$.diethylaniline; aluminium hydrides such as aluminium hydride (alane), $LiAlH_4$, $^iBu_2AlH$, sodium bis(2-methoxyethoxy)aluminium hydride (Red-Al) or $LiHAl(OCH_3)_2$, optionally in the presence of one or more Lewis acids, such as trifluoroborane, titanium chloride, aluminium chloride, zinc iodide or trifluoroacetic acid. The preferred reducing agent is a silane, more preferably triethylsilane or diphenylsilane, optionally in the presence of one o more Lewis acids, such as trifluoroborane, also in form of complexes with ethers, such as boron trifluoride diethyl etherate, titanium chloride, aluminium chloride, zinc iodide or trifluoroacetic acid. More preferably, the reduction of the desmethyl-lactam (XVII) into desmethylasenapine (XVIII) is carried out by using triethylsilane in the presence of boron trifluoride diethyl etherate.

The reduction of the desmethyl-lactam (XVII) into desmethylasenapine (XVIII) as disclosed herein can take place in the absence of any solvent or in the presence of an organic solvent. Non-limiting examples of suitable organic solvents which can be used are: ethers such as tetrahydrofuran, dioxane, diisopropylether, diethylether, 2-methyltetrahydrofuran, cyclopentyl methyl ether or methyl tert-butyl ether; halogenated solvents such as dichloromethane, chloroform, tetrachloromethane, dichloroethane, chlorobenzene or dichlorobenzene; hydrocarbon aliphatic solvents such as methylcyclohexane, cyclohexane, heptane or hexane; hydrocarbon aromatic solvents such as toluene, benzene, o-xylene, m-xylene or p-xylene, or mixtures of two or more of the solvents listed. Preferably, the reduction of the desmethyl-lactam (XVII) into desmethylasenapine (XVIII) as disclosed herein takes place in the absence of any solvent.

The molar ratio of the reducing agent with respect to the desmethyl-lactam (XVII) in the reduction of the desmethyl-lactam (XVII) into desmethylasenapine (XVIII) as disclosed herein is from about 1 to about 10, preferably from about 2 to about 6, more preferably about 5.

The reduction of the desmethyl-lactam (XVII) into desmethylasenapine (XVIII) as disclosed herein can take place at a temperature from about −20° C. to about 250° C., preferably from about 20° C. to about 200° C., more preferably from about 50° C. to about 150° C., and even more preferably from about 100° C. to about 110° C.

In a preferred embodiment of the present invention the reduction of the desmethyl-lactam (XVII) into desmethylasenapine (XVIII) is carried out by using triethylsilane in the presence of boron trifluoride diethyl etherate, with a molar ratio of triethylsilane with respect to desmethyl-lactam (XVII) of about 5, in the absence of any solvent at about 105° C.

Alternatively, reduction of desmethyl-lactam (XVII) into desmethylasenapine (XVIII) can also be carried out by transforming the desmethyl-lactam (XVII) into desmethyl-thiolactam and reducing it into desmethylasenapine (XVIII). The desmethyl-thiolactam can be obtained, for example, directly by reaction of the desmethyl-lactam (XVII) with sulfur-containing reagents such as Lawesson's reagent, i.e. 2,4-bis(4-methoxyphenyl)-1,3,2,4-dithiadiphosphetane-2,4-disulfide, bis(tricyclohexyltin)sulfide, hydrogen sulfide, or phosphorus pentasulfide ($P_4S_{10}$). The reduction of the desmethyl-thiolactam can be performed similarly as the above disclosed reduction of the desmethyl-lactam (XVII) or in the presence of Raney nickel.

The desmethylasenapine (XVIII) obtained after the reduction of the desmethyl-lactam (XVII) as disclosed herein can be isolated as a base or as a salt, which includes salts with inorganic acids such as hydrochloride, hydrobromide, nitrate, phosphate and sulphate, and salts with organic acids such as acetate, fumarate, oxalate, maleate, citrate, malate, methanesulfonate, benzenesulphonate, tosylate, tartrate, lactate, benzoate, succinate, malonate, adipate, ascorbate or propionate. Alternatively, the desmethylasenapine (XVIII) obtained after the reduction of the desmethyl-lactam (XVII) as disclosed herein can be further used in the following methylation step without isolation.

Transformation of desmethylasenapine (XVIII) into compound trans-(I) as disclosed herein can be carried out using a methylating agent. As used herein, the term "methylating agent" refers to a reagent or mixtures of reagents that can be used for covalent attaching a methyl group to a nitrogen atom. Examples of methylation reagents include but are not limited to: dimethylsulfate, methyl iodide, methyl chloride, methyl bromide, mixtures of formaldehyde and formic acid and mixtures of formaldehyde and sodium triacetoxyborohydride.

Transformation of desmethylasenapine (XVIII) into compound trans-(I) with retention of the trans configuration as used herein is preferably carried out by using a mixture of formaldehyde and formic acid as described in the literature (EP 2166012 A1 (US 2011/0046393), the subject matter of which is incorporated herein by reference). This transformation can also be preferably carried out using a mixture of formaldehyde and sodium triacetoxyborohydride, as described in WO 2009/087058 (U.S. Pat. No. 7,964,739), the subject matter of which is incorporated herein by reference.

The transformation of desmethylasenapine (XVIII) into compound trans-(I) as disclosed herein can take place in the absence of any solvent or in the presence of an organic solvent. Non-limiting examples of suitable organic solvents which can be used are: ethers such as tetrahydrofuran, dioxane, diisopropylether, diethylether, 2-methyltetrahydrofuran, cyclopentyl methyl ether or methyl tert-butyl ether; halogenated solvents such as dichloromethane, chloroform, tetrachloromethane, dichloroethane, chlorobenzene or dichlorobenzene; hydrocarbon aliphatic solvents such as methylcyclohexane, cyclohexane, heptane or hexane; hydrocarbon aromatic solvents such as toluene, benzene, o-xylene, m-xylene or p-xylene, or mixtures of two or more of the solvents listed. Preferably, the transformation of desmethylasenapine (XVIII) into compound trans-(I) as disclosed herein takes place in a hydrocarbon aromatic solvent such as toluene, benzene, o-xylene, m-xylene or p-xylene, more preferably in toluene.

In a preferred embodiment of the present invention the transformation of desmethylasenapine (XVIII) into compound trans-(I) is carried out using a mixture of formic acid and formaldehyde, preferably an aqueous solution of formaldehyde, as methylating agent in toluene as organic solvent at a temperature about 60° C.

The present invention provides a process for preparing the desmethyl-lactam (XVII) comprising the ring-closing of the amino-ester (XII') or the amino-acid (XVI),

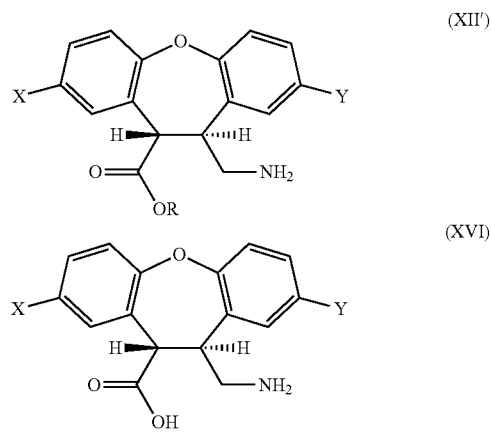

wherein the ring-closing is carried out in the presence of any acidic catalyst or any mild basic catalyst.

wherein X is H and Y is Cl or wherein X is Cl and Y is H and R is any alkyl, optionally substituted; benzyl, optionally substituted or phenyl, optionally substituted. Preferably, R is a $C_1$-$C_6$ alkyl, optionally substituted. More preferably R is methyl.

The ring closing of the amino-ester (XII') or the amino-acid (XVI) under these conditions reduces the isomerization of trans-(XVII) into undesired cis-(XVII).

By the term "acidic catalyst" as used herein is meant a substance which is a proton donor or a substance which in its environment will form or become a proton donor. All acids are operable as an acidic catalyst in this invention, for example, Brønsted acids such as mineral and carboxylic acids, or Lewis acids. Non-limiting examples of a Lewis acid are zinc chloride, ferrous chloride, tin chloride, aluminum chloride, barium fluoride, and sulfur trioxide. Other example of acidic catalysts are quaternary ammonium salts having at least one proton substituent. The carboxylic acid group of unreacted amino-acid (XVI) during the cyclization reaction can also act as acidic catalyst according to the present invention. The acidic catalyst as used herein comprises any acidic compound having a $pK_a$ equal or less than 7.

The term "in the presence of any mild basic catalyst" as used herein refers that the strongest base with affinity for hydrogen present in the cyclization reaction mixture has a $pK_a$ value below 16. Preferred mild basic catalysts are hydroxides such as lithium, sodium or potassium hydroxide; carbonates such as lithium carbonate, sodium carbonate, potassium carbonate or cesium carbonate; hydrogencarbonates such as sodium hydrogencarbonate; primary, secondary or tertiary amines or anilines. The amino group of unreacted amino-ester (XII') or amino-acid (XVI) during the cyclization reaction can also act as mild basic catalyst according to the present invention. Preferably the mild basic catalyst used in the ring-closing reaction is the unreacted amino-ester (XII'), the unreacted amino-acid (XVI) or sodium or potassium hydroxide.

The $pK_a$ is a measurement of the strength of an acid. The lower the $pK_a$, the stronger the acidity. The higher the $pK_a$, the weaker the acid. The $pK_b$ is a related measurement and is a measurement of the strength of a base; the lower the $pK_b$, the stronger the base and the higher the $pK_b$, the weaker the base. Although it is not strictly accurate, often the $pK_a$ of a base's conjugated acid is provided as the $pK_a$ of the base. In this application the term $pK_a$ of a base is used to designate the $pK_a$ of the base's conjugated acid. In this application the $pK_a$ values refer to the $pK_a$ in water as determined at room temperature and atmospheric pressure.

The term "alkyl, optionally substituted" as used herein refers to branched or straight chained alkyl group. Such an alkyl group may be optionally substituted, so that one or more of its hydrogen atoms are replaced by a substituent selected from the group consisting of halogen, thiol, cyano, phenyl, $OR_1$, and $NR_2R_3$, in which $R_1$, $R_2$ and $R_3$ are each independently represented by hydrogen or alkyl.

The term "$C_1$-$C_6$ alkyl, optionally substituted" as used herein refers to a branched or straight chained alkyl group containing from 1 to 6 carbon atoms, such as methyl, ethyl, n-propyl, isopropyl, n-butyl, isobutyl, pentyl, etc. Such an alkyl group may be optionally substituted, so that one or more of its hydrogen atoms are replaced by a substituent selected from the group consisting of halogen, thiol, cyano, phenyl, $OR_1$, and $NR_2R_3$, in which $R_1$, $R_2$ and $R_3$ are each independently represented by hydrogen or alkyl.

The term "benzyl, optionally substituted" as used herein refers to a benzyl group which may be optionally substituted, so that one or more of its hydrogen atoms are replaced by a substituent selected from the group consisting of halogen, thiol, cyano, phenyl, $OR_1$, and $NR_2R_3$, in which $R_1$, $R_2$ and $R_3$ are each independently represented by hydrogen or alkyl.

The term "phenyl, optionally substituted" as used herein refers to a phenyl group which may be optionally substituted, so that one or more of its hydrogen atoms are replaced by a substituent selected from the group consisting of halogen, thiol, cyano, phenyl, $OR_1$, and $NR_2R_3$, in which $R_1$, $R_2$ and $R_3$ are each independently represented by hydrogen or alkyl.

In a preferred embodiment of the present invention, the desmethyl-lactam (XVII) is obtained by a process comprising the ring-closing of the amino-ester (XII') wherein the ring-closing of the amino-ester (XII') is catalyzed by the unreacted amino-ester (XII') which acts as a mild basic catalyst for the cyclization reaction.

In another preferred embodiment of the present invention, the desmethyl-lactam (XVII) is obtained by a process comprising the ring-closing of the amino-acid (XVI) wherein the ring-closing of the amino-acid (XVI) is catalyzed by the unreacted amino-acid (XVI) which acts as a mild basic catalyst (the amino group) or as an acidic catalyst (the carboxylic acid group) for the cyclization reaction.

In another preferred embodiment of the present invention, the desmethyl-lactam (XVII) is obtained by a process comprising the ring-closing of the amino-ester (XII') or the ring-closing of the amino-acid (XVI) wherein the ring-closing of the amino-ester (XII') or the amino-acid (XVI) is catalyzed by sodium or potassium hydroxide.

The ring-closing of the amino-ester (XII') or the amino-acid (XVI) to give the desmethyl-lactam (XVII) as disclosed herein takes place preferably in the presence of an organic solvent or mixtures of an organic solvent and water. Non-limiting examples of suitable organic solvents which can be used are: alcohols such as methanol, ethanol, isopropanol, n-propanol, n-butanol, isobutanol, sec-butanol or tert-butanol; ketones such as acetone, methyl ethyl ketone or methyl isobutyl ketone; ethers such as tetrahydrofuran, dioxane, diisopropylether, diethylether, 2-methyltetrahydrofuran, cyclopentyl methyl ether or methyl tert-butyl ether; esters such as ethyl acetate, methyl acetate, isopropyl acetate, n-propyl acetate, n-butyl acetate, isobutyl acetate, sec-butyl acetate or tert-butyl acetate; halogenated solvents such as dichloromethane, chloroform, tetrachloromethane, dichloroethane, chlorobenzene or dichlorobenzene; polar aprotic solvents such as N,N-dimethylformamide, acetonitrile, N,N-dimethylacetamide, N-methyl-2-pyrrolidone or dimethylsulfoxide; hydrocarbon aliphatic solvents such as methylcyclohexane, cyclohexane, heptane or hexane; hydrocarbon aromatic solvents such as toluene, benzene, o-xylene, m-xylene or p-xylene; or mixtures of two or more of the solvents listed. Preferred organic solvents used for the ring-closing of the amino-ester (XII') or the amino-acid (XVI) to give the desmethyl-lactam (XVII) as disclosed herein are esters, more preferably ethyl acetate, wherein the unreacted amino-ester (XII') or the amino-acid (XVI) acts as a catalyst for the cyclization reaction; or alcohols, more preferably methanol, when sodium or potassium hydroxide is used as a mild basic catalyst.

The molar ratio of the mild basic catalyst, preferably sodium or potassium hydroxide, with respect to the amino-ester (XII') or the amino-acid (XVI) in the ring-closing of the amino-ester (XII') or the amino-acid (XVI) to give the desmethyl-lactam (XVII) as disclosed herein is from about 0.01 to about 2, preferably from about 0.1 to about 1, more preferably about 0.6.

The ring-closing of the amino-ester (XII') or the amino-acid (XVI) to give the desmethyl-lactam (XVII) as disclosed herein takes place at a temperature from about −10° C. to about 200°, more preferably from about 0° C. to about 100° C., more preferably from about 20° C. to about 30° C.

The amino-acid (XVI) can be obtained by hydrolysis of the amino-ester (XII') using known methods in the art, such as hydrolysis under acidic or basic conditions. The hydrolysis under basic conditions is particularly preferred since it can help to isomerize undesired cis-(XVI) into trans-(XVI). Amino-acid (XVI) is then cyclized to desmethyl-lactam (XVII).

Alternatively, the desmethyl-lactam (XVII) can be also obtained by the ring-closing of the amino-acid (XVI) by means of the activation of the carboxylic acid followed by intramolecular formation of the amide bond.

The activation of the carboxylic acid as used herein involves the use of suitable agents for the activation of carboxylic acids in the formation of amides such as thionyl chloride, N,N'-carbonyldiimidazole (CDI), dicyclohexylcarbodiimide (DCC), diisopropylcarbodiimide (DIC), 1-ethyl-3-(3'-dimethylaminopropyl)carbodiimide (EDC or WSC), 1-propanephosphonic acid cyclic anhydride (T3P), 2-(7-aza-1H-benzotriazole-1-yl)-1,1,3,3-tetramethyluronium hexafluorophosphate (HATU), 2-(1H-benzotriazole-1-yl)-1,1,3,3-tetramethyluronium hexafluorophosphate (HBTU), 2-(6-chloro-1H-benzotriazole-1-yl)-1,1,3,3-tetramethylaminium hexafluorophosphate (HCTU), 2-(1H-benzotriazole-1-yl)-1,1,3,3-tetramethyluronium tetrafluorophosphate (TBTU), benzotriazole-1-yl-oxytris(dimethylamino)phosphonium hexafluorophosphate (BOP), benzotriazole-1-yl-oxytrispyrrolidinophosphonium hexafluorophosphate (PyBOP), (1-cyano-2-ethoxy-2-oxoethylidenaminooxy)dimethylaminomorpholinocarbenium hexafluorophosphate (COMU), or mixtures thereof. Preferred agents for the activation of carboxylic acids in the formation of amides is thionyl chloride.

The amino-ester (XII') as disclosed herein is preferably obtained by a process comprising:
(a) reducing the nitro-ester (XI'),

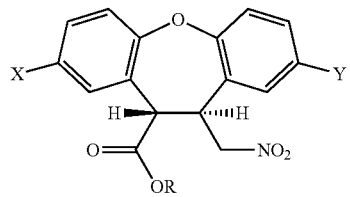
(XI')

to give amino-ester (XII'),

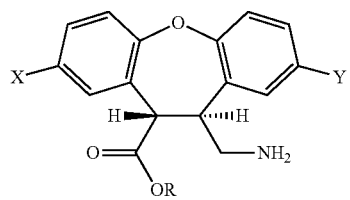
(XII')

wherein X is H and Y is Cl or wherein X is Cl and Y is H and R is any alkyl, optionally substituted; benzyl, optionally substituted or phenyl, optionally substituted. Preferably, R is a $C_1$-$C_6$ alkyl, optionally substituted. More preferably R is methyl.

Optionally the amino-ester (XII') can be hydrolyzed into the amino-acid (XVI),

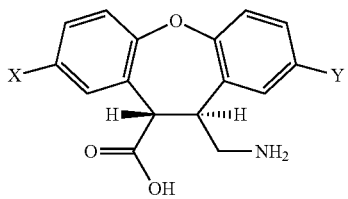
(XVI)

The reduction of the nitro-ester (XI') to the amino-ester (XII') can be carried out by means of any of the known methods in the art, such as catalytic hydrogenation, catalyzed hydrogen transfer reaction, nascent hydrogen conditions (reducing metals in the presence of acidic reagents), and use of reducing borohydride or aluminium hydride reagents (after protection of the ester moiety).

The amino-ester (XII') as well as the amino-acid (XVI) as disclosed herein can be in form of base or salts thereof. Suitable salts of the amino-ester (XII') comprise salts with inorganic acids such as hydrochloride, hydrobromide, nitrate, phosphate and sulphate; or salts with organic acids such as acetate, fumarate, oxalate, maleate, citrate, malate, methanesulfonate, benzenesulphonate, tosylate, tartrate, lactate, benzoate, succinate, malonate, adipate, ascorbate or propionate. Suitable salts of the amino-acid (XVI) comprise salts with inorganic acids such as hydrochloride, hydrobromide, nitrate, phosphate and sulphate; salts with organic acids such as acetate, fumarate, oxalate, maleate, citrate, malate, methanesulfonate, benzenesulphonate, tosylate, tartrate, lactate, benzoate, succinate, malonate, adipate, ascorbate or propionate; salts with metals such as sodium, potassium, calcium and aluminium; or salts with amines such as N,N-diisopropylethylamine (DIPEA), trimethylamine, tripropylamine, triethylamine, N-methylpiperidine, N,N-dimethylaminopyridine (DMAP), N-methylpyrrolidine and 1,4-diazabicyclo[2.2.2]octane (DABCO).

In another aspect of the present invention, compound trans-(I) or a salt thereof can be obtained by a process comprising any of the processes for preparing the desmethyl-lactam (XVII) disclosed above.

In another aspect of the present invention, compound trans-(I) or a salt thereof can be obtained by a process comprising:
(a) reducing the nitro-ester (XI'),

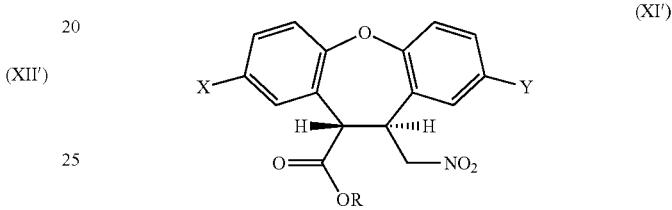
(XI')

to give the amino-ester (XII'),

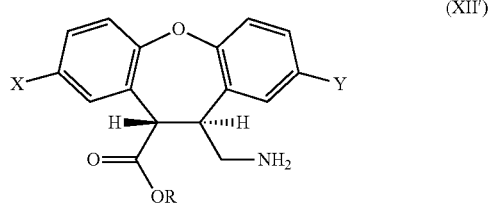
(XII')

(b) optionally hydrolyzing the amino-ester (XII') into the amino-acid (XVI),

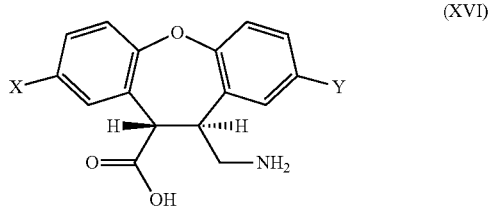
(XVI)

(c) performing the ring-closing of the amino-ester (XII') or the amino-acid (XVI),

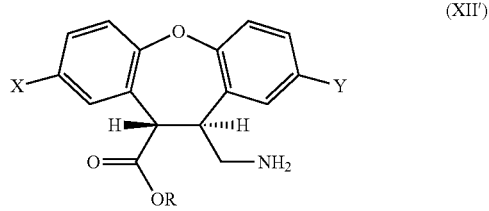
(XII')

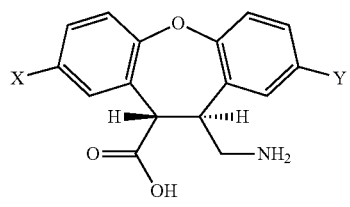

(XVI)

to give the desmethyl-lactam (XVII)

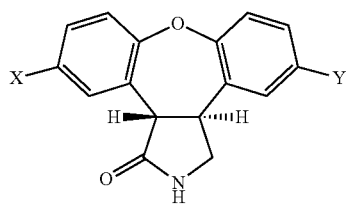

(XVII)

(d) reducing desmethyl-lactam (XVII) to give desmethylasenapine (XVIII)

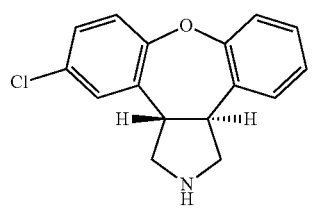

(XVIII)

(e) methylating desmethylasenapine (XVIII) to give compound trans-(I); and (f) optionally converting compound trans-(I) to a salt thereof, wherein X is H and Y is Cl or wherein X is Cl and Y is H and R is any alkyl, optionally substituted; benzyl, optionally substituted or phenyl, optionally substituted. Preferably, R is a $C_1$-$C_6$ alkyl, optionally substituted. More preferably R is methyl.

In another aspect of the present invention, compound trans-(I) or a salt thereof can be obtained with reduced formation of undesired cis isomers by a process comprising:

(a) methylating desmethyl-lactam (XVII),

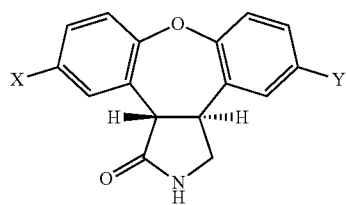

(XVII)

to give lactam (VI),

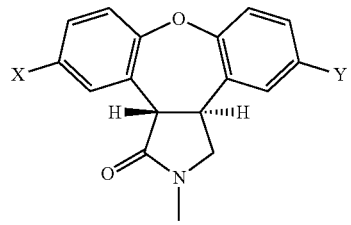

(VI)

wherein methylation is performed using mild bases, formaldehyde in the presence of trifluoroacetic acid and/or triethylsilane.

(b) reducing lactam (VI) to give compound trans-(I); and (c) optionally converting compound trans-(I) to a salt thereof, wherein X is H and Y is Cl or wherein X is Cl and Y is H.

As used herein, the term "mild base" refers to a base having a $pK_a$ of about 16 or less, preferably about 12 to about 7, more preferably about 12 to about 9. Preferred bases are selected from the group consisting of ammonia, mono-, di- or tri-alkylamines (preferably wherein each alkyl group contains from 1 to 6 carbon atoms and more preferably from 1 to 3 carbon atoms, and more preferably is methyl or ethyl), alkali metal carbonates, alkaline-earth metal carbonates, alkali metal bicarbonates, and alkaline earth metal bicarbonates, and combinations thereof. More preferred are the alkali metal carbonates and alkali metal bicarbonates, most preferably sodium and potassium carbonate and sodium and potassium bicarbonate.

The authors of the present invention have found that compound trans-(I) can be obtained mainly with the desired trans configuration without the need of carrying out any of the low-yield processes for the conversion of undesired cis-(VI) to trans-(VI) described in EP 1710241 B1.

The use of strong bases for the conversion of trans-(XII) to trans-(VI), such as the described use of potassium tert-butoxide in EP 1710241 B1, has been found to be particularly detrimental since it helps to the isomerization of the trans compounds into the thermodynamically more stable and undesired cis ones. The authors of the present invention have found that the use of mild bases (i.e. a basic compound having a $pK_a$ value below 16) is therefore preferred for this transformation. Alternative methods known which avoid the use of basic reagents, such as the use of formaldehyde in the presence of trifluoroacetic acid and/or triethylsilane, are also preferred for this transformation.

Transformation of lactam (VI) into compound trans-(I) is described in the literature, for example in Example 6 of EP 1710241 B1 by using lithium aluminium hydride in the presence of aluminium chloride. Alternative methods are the use of borane reagents, sodium bis(2-methoxyethoxy)aluminium hydride (Red-Al), triethylsilane in the presence of a metal catalyst, and/or sodium borohydride in the presence of trifluoroborane, are also particularly preferred for this transformation.

The processes of the present invention, summarized in scheme 5, allow the conversion of the nitro-ester trans-(XI') into compound trans-(I) with a minimum formation of undesired cis-(I).

Scheme 5

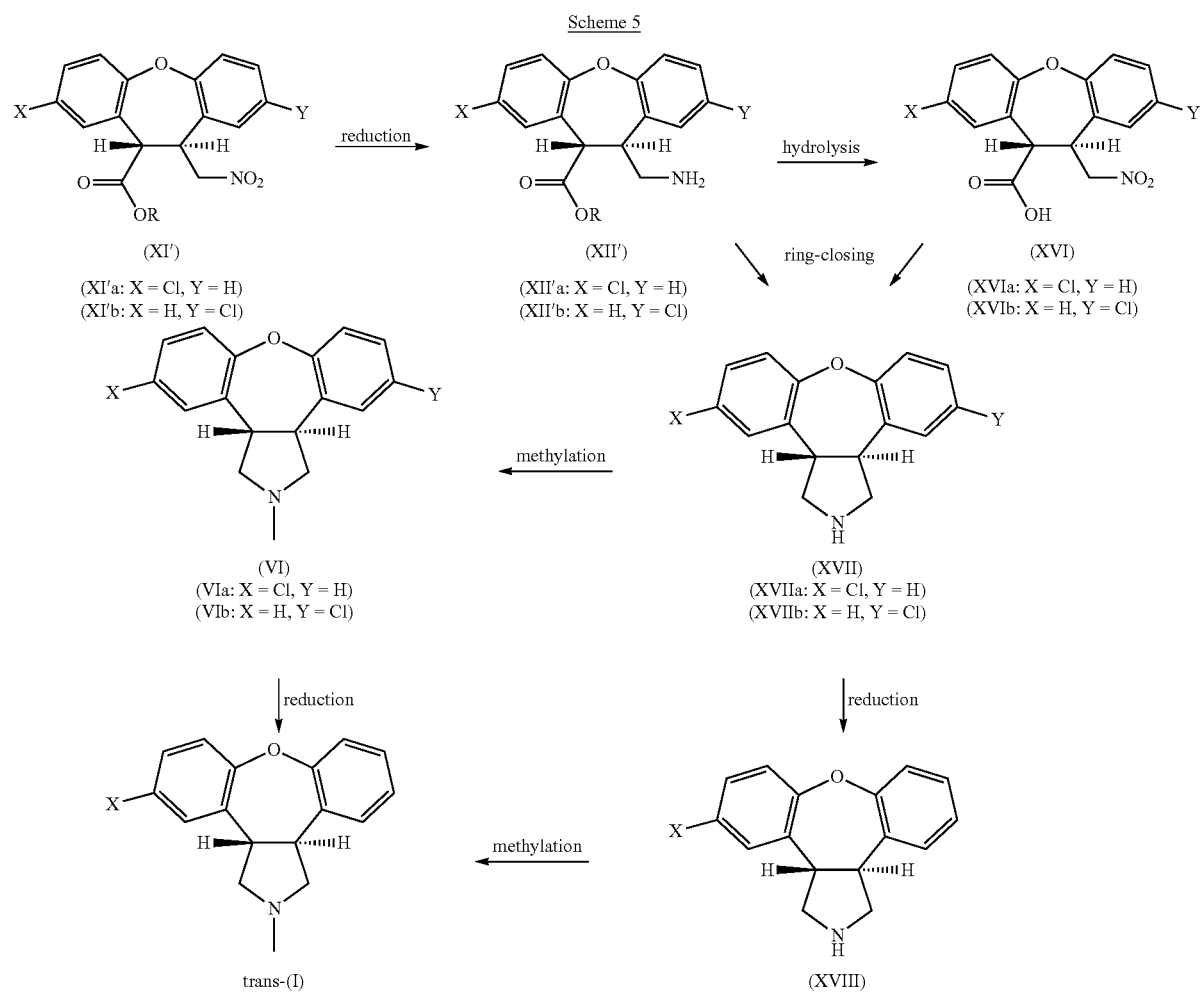

wherein R is any alkyl, optionally substituted; benzyl, optionally substituted or phenyl, optionally substituted. Preferably, R is a $C_1$-$C_6$ alkyl, optionally substituted. More preferably R is methyl.

In another aspect, the present invention provides a process for preparing compound trans-(I) or a salt thereof comprising an alternative process for the synthesis of lactam (VI), which avoids the problems related to the magnesium/methanol reduction of enamide (V) disclosed in the prior art. The process for the synthesis of lactam (VI) is summarized in Scheme 6 below.

Scheme 6

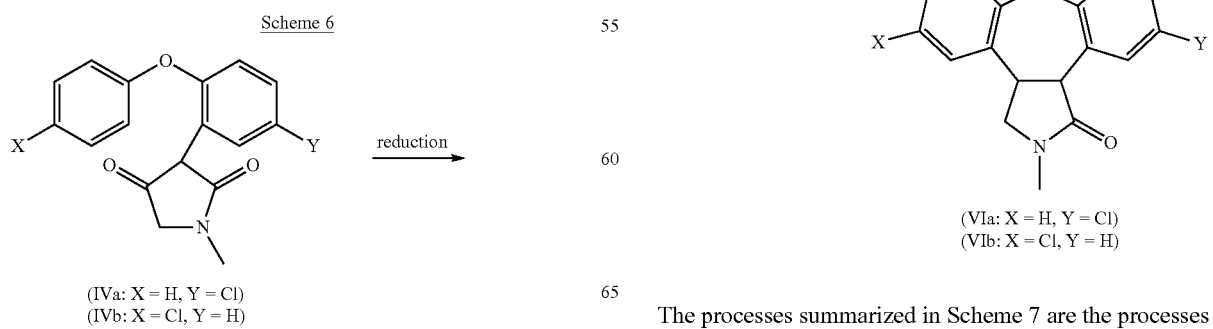

The processes summarized in Scheme 7 are the processes particularly preferred for the synthesis of lactam (VI).

Scheme 7
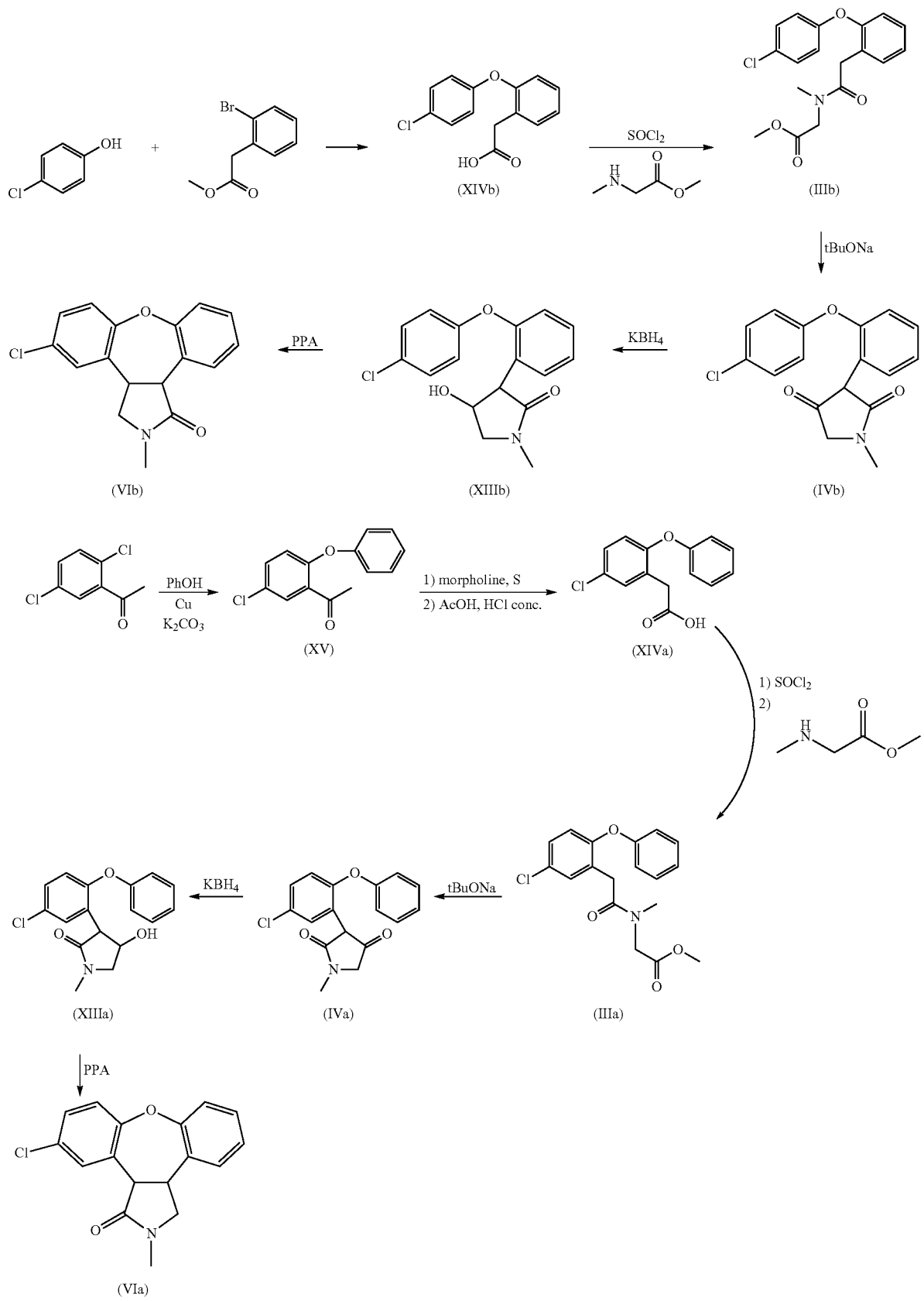

The reduction of compounds (IVa) or (IVb) can be carried out by any known method in the art for the reduction of ketones to alcohols, such as catalytic hydrogenation, reduction by metals (e.g. lithium, sodium, potassium, magnesium, aluminium, zinc, iron), metal hydride reduction (e.g. lithium or sodium hydride), borohydride reduction (e.g. lithium, sodium, potassium, calcium or zinc borohydride), cyanoborohydride reduction (e.g. lithium, sodium or potassium cyanoborohydride), triacetoxyborohydride reduction (e.g. sodium or potassium triacetoxyborohydride), trialkoxyborohydride reduction (e.g. sodium or potassium trimethoxyborohydride, triisopropoxyborohydride or tri-tert-butoxyborohydride), trialkylborohydride reduction (e.g. lithium or potassium triethylborohydride or tri-sec-butylborohydride), triarylborohydride reduction (e.g. potassium triphenylborohydride), aluminium hydride reduction (e.g. diisobutylaluminium hydride, lithium or sodium aluminium hydride, lithium trimethoxyaluminium hydride, lithium tri-tert-butoxyaluminium hydride), silane reduction (e.g. triethylsilane, dimethylphenylsilane, triphenylsilane), borane reduction ($BH_3$), alkylborane reduction (e.g. dicyclohexylborane, diisopinocamphenylborane, 9-borabicyclo(3.3.1)nonane), Meerwein-Ponndorf-Verley reduction (e.g. triisopropoxyaluminium and isopropanol), hydrosulfite reduction, electrolytic reduction and enzymatic reduction. Use of borohydride reagents is preferred, and potassium borohydride is particularly preferred.

The cyclization of compounds (XIIIa) or (XIIIb) can be carried out by using any dehydrating agent known in the art, such as stirring in the presence of concentrated sulfuric acid, pyrophosphoric acid or polyphosphoric acid.

As used herein, the term "dehydrating agent" means a mild chemical compound which removes the water released during the cyclization of compound (XIIIa) or (XIIIb). Known dehydrating agents such as sulfuric acid, pyrophosphoric acid, polyphosphoric acid and phosphorus pentoxide are suitable.

Compounds (VIa) or (VIb) can be obtained having a favorable cis/trans ratio. Desired trans-(VI) can be isolated by any method known in the art, such as selective crystallization or chromatographic purification. Undesired cis-(VI) can be converted into desired trans-(VI) by any method known in the art, such as isomerization under basic conditions (e.g. using 1,5-diazabicyclo[4.3.0]non-5-ene (DBN), as described in the European Patent EP 1710241 B1) or a ring-opening step followed by isomerization and ring-closing as described in the European Patent EP 1710241 B1.

Transformation of lactams trans-(Via) or trans-(VIb) into asenapine trans-(I) is described in the literature, for example in Example 6 of EP 1710241 B1 by using lithium aluminium hydride in the presence of aluminium chloride. Alternative methods known in the art such as use of borane reagents, sodium bis(2-methoxyethoxy)aluminium hydride (Red-Al), triethylsilane in the presence of a metal catalyst, and/or sodium borohydride in the presence of trifluoroborane, are also particularly preferred for this transformation.

In one embodiment of the present invention the processes for preparing compound trans-(I) further comprises the conversion of the undesired compound cis-(VI) to the desired compound trans-(VI).

The compound trans-(I) obtained by the processes disclosed herein can be optionally converted to a salt thereof. Suitable salts of compound trans-(I) can be obtained from the treatment with a mineral acid such as hydrochloric acid, hydrobromic acid, nitric acid, phosphoric acid and sulfuric acid, or with an organic acid such as for example ascorbic acid, citric acid, tartaric acid, lactic acid, maleic acid, oxalic acid, malic acid, malonic acid, fumaric acid, glycolic acid, succinic acid, propionic acid, acetic acid, benzene sulphonic acid, toluene sulphonic acid, and methane sulfonic acid. The preferred acid addition salt of compound trans-(I) is the maleate salt.

The term "about" when used in the present invention preceding a number and referring to it, is meant to designate any value which lies within the range defined by the number ±10% of its value, preferably a range defined by the number ±5%, more preferably range defined by the number ±2%, still more preferably a range defined by the number ±1%. For example "about 10" should be construed as meaning within the range of 9 to 11, preferably within the range of 9.5 to 10.5, more preferably within the range of 9.8 to 10.2, and still more preferably within the range of 9.9 to 10.1.

EXPERIMENTAL EXAMPLES

HPLC Method 1:

The chromatographic separation was carried out in a Kromasil 100-5 C18, 5 µm, 4.6×250 mm column at 25° C.

The mobile phase was a filtered and degassed acetonitrile/buffer (60:40) v/v mixture. The buffer was a water/triethylamine/acetic acid (265:5:4) v/v/v mixture.

The chromatograph was equipped with a 254 nm detector and the flow rate was 1.0 mL per minute. 20 µL of the test samples were injected. The test samples were prepared by dissolving the appropriate amount of sample in mobile phase, to obtain a concentration of about 1.0 mg per mL. The chromatogram was run for at least 20 min. The approximate retention time for asenapine was found to be 4 min.

HPLC Method 2:

The chromatographic separation was carried out in a Kromasil 100 C18, 5 µm, 4.6×250 mm column at 30° C.

The mobile phase A was water containing 0.1% (w/w) methanesulfonic acid. pH was adjusted to 2.5 with diethylamine.

The mobile phase B was acetonitrile.

The chromatograph was programmed as follows: Initial 0-3 min. 75% mobile phase A, 3-50 min. linear gradient to 35% mobile phase A, 50-55 min. isocratic 35% mobile phase A, 55-70 min. linear gradient to 10% mobile phase A, 70-100 min. isocratic 10% mobile phase A, 100-105 min. linear gradient to 75% mobile phase A, 105-110 min. isocratic 75% mobile phase A.

The chromatograph was equipped with a 210 nm detector and the flow rate was 1.0 mL per minute. 10 µL of the test samples were injected. The test samples were prepared by dissolving the appropriate amount of sample in methanol, to obtain a concentration of about 0.5 mg per mL. The chromatogram was run for at least 100 min. The approximate retention time for trans-5-chloro-2,3,3a,12b-tetrahydro-1H-dibenzo[2,3:6,7]oxepino[4,5-c]pyrrole (compound trans-XVIII) was found to be 16.7 min.

Example 1

Synthesis of 2-(4-chlorophenoxy)phenylacetic acid (compound XIVb)

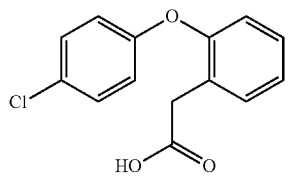 [SMILES: O=C(O)Cc1ccccc1Oc1ccc(Cl)cc1]

27.8 g (216 mmol) of 4-chlorophenol and 47 g (205 mmol) of methyl 2-bromophenylacetate were suspended in 790 mL of dioxane. The mixture was heated to 48° C. and 141 g of cesium carbonate, 4.5 g of glycine and 8.6 g of cuprous chloride were added. The resulting suspension was heated to reflux and stirred at this temperature for 5 days. After cooling down to room temperature, the solid was removed by filtration, washed with 100 mL of dioxane, and discarded. The mother liquors were combined and concentrated under vacuum. 100 mL of ethyl acetate were added to the residue, and the pH was adjusted to 1 with HCl 2 M. The organic phase was extracted, washed with brine and dried. The solvent was removed under vacuum. 100 mL of water were added to the residue, and the pH was adjusted to 1 with HCl 2 M. The resulting suspension was stirred and filtered, to obtain 41 g of 2-(4-chlorophenoxy)phenylacetic acid (compound XIVb) as a brown solid. Yield: 76.1%.

Example 2

Synthesis of methyl N-{2-[2-(4-chlorophenoxy)phenyl]-1-oxoethyl}-N-methylglycinate (compound IIIb)

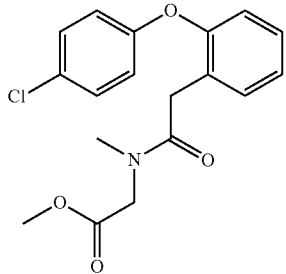 [SMILES: COC(=O)CN(C)C(=O)Cc1ccccc1Oc1ccc(Cl)cc1]

20 g (76.1 mmol) of 2-(4-chlorophenoxy)phenylacetic acid (compound XIVb) were dissolved in 200 mL of toluene under reflux temperature. After cooling to 50° C., 8.4 mL of thionyl chloride were added dropwise and the resulting mixture was stirred at 50° C. for 1 hour. After cooling down to room temperature, the solvent was removed under vacuum. 50 mL of fresh toluene were added to the residue, and were distilled under vacuum. The residue was dissolved in 20 mL of fresh toluene, and the resulting solution was added dropwise over a second flask containing a mixture of 12.8 g of sarcosine hydrochloride, 150 mL of N,N-dimethylformamide, 50 mL of toluene and 26 mL of triethylamine, previously cooled to 5° C. The resulting mixture was stirred at 5° C. for 10 minutes, warmed to room temperature and stirred at this temperature for 2 hours. 300 mL of water were added. The aqueous phase was extracted and washed twice with 300 mL of ethyl acetate. The organic phases were combined, washed with brine, dried and concentrated under vacuum, to obtain 27.8 g of methyl N-{2-[2-(4-chlorophenoxy)phenyl]-1-oxoethyl}-N-methylglycinate (compound IIIb) as an oil.

Example 3

Synthesis of 3-[2-(4-chlorophenoxy)phenyl]-1-methylpyrrolidine-2,4-dione (compound IVb)

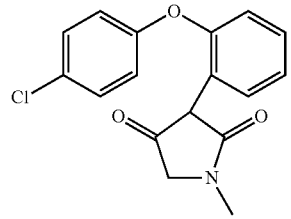 [SMILES: CN1CC(=O)C(c2ccccc2Oc2ccc(Cl)cc2)C1=O]

27.8 g (79.9 mmol) of methyl N-{2-[2-(4-chlorophenoxy)phenyl]-1-oxoethyl}-N-methylglycinate (compound IIIb) was dissolved in 150 mL of toluene. 11.5 g of sodium tert-butoxyde were added, and the resulting mixture was stirred overnight at room temperature. 350 mL of water were added, and the resulting mixture was extracted three times with 150 mL of ethyl acetate. The combined organic phases were washed with 200 mL of water. The aqueous phases were combined and pH was adjusted to 1 with HCl 2 M. The solvent was removed by filtration, and the solid was recrystallized twice with methanol, to obtain 5.4 g of 3-[2-(4-chlorophenoxy)phenyl]-1-methylpyrrolidine-2,4-dione (compound IVb) as a solid. Yield: 21.4%.

$^1$H-NMR (400 MHz, DMSO-$d_6$, 25° C.) δ (ppm): 11.06 (broad s), 7.36 (m, 4 H), 7.15 (dd, 1 H, J=7.2 Hz, J=7.2 Hz), 6.94 (d, 2 H, J=8.8 Hz), 6.88 (d, 1 H, J=8.0 Hz), 3.81 (s, 2 H), 2.80 (s, 3 H). $^{13}$C-NMR (100.6 MHz, DMSO-$d_6$, 25° C.) δ (ppm): 170.8, 166.4, 156.1, 154.4, 132.2, 129.4, 128.4, 126.4, 123.5, 123.3, 119.9, 118.8, 102.3, 51.2, 28.3.

Example 4

Synthesis of 3-[2-(4-chlorophenoxy)phenyl]-4-hydroxy-1-methylpyrrolidine-2-one (compound XIIIb)

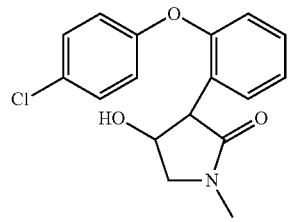 [SMILES: CN1CC(O)C(c2ccccc2Oc2ccc(Cl)cc2)C1=O]

5 g (15.8 mmol) of 3-[2-(4-chlorophenoxy)phenyl]-1-methylpyrrolidine-2,4-dione (compound IVb) was dissolved in a mixture of 150 mL of tetrahydrofuran and 15 mL of water. The solution was cooled to 0° C., and 4.3 g of potassium borohydride were added slowly, keeping the temperature below 10° C. The resulting solution was stirred at 0° C. for 6 hours. Then, a saturated solution of ammonium chloride was added, and the pH was adjusted to 3 with HCl 2 M. 100 mL of ethyl acetate were added. The organic phase was extracted, washed with saturated sodium bicarbonate and with water, dried and concentrated under vacuum, to obtain 4.5 g of 3-[2-(4-chlorophenoxy)phenyl]-4-hydroxy-1-methylpyrrolidine-2-one (compound XIIIb) as a sticky solid. Yield: 89.6%.

¹H-NMR (400 MHz, DMSO-d₆, 25° C.) δ (ppm): 7.39 (dm, 2 H, J=10.0 Hz), 7.28 (m, 2 H), 7.14 (dd, 1 H, J=7.6 Hz, J=7.6 Hz, J=1.2 Hz), 6.98 (dm, 2 H, J=8.8 Hz), 6.88 (dd, 1 H, J=8.0 Hz, J=1.2 Hz), 5.05 (d, 1 H, J=4.8 Hz), 4.26 (dm, 1 H, J=4.8 Hz), 3.94 (d, 1 H, J=6.0 Hz), 3.61 (dd, 1 H, J=10.4 Hz, J=4.8 Hz), 3.17 (dd, 1 H, J=10.4 Hz, J=0.8 Hz), 2.78 (s, 3 H). ¹³C-NMR (100.6 MHz, DMSO-d₆, 25° C.) δ (ppm): 172.2, 156.6, 154.5, 133.3, 129.6, 128.2, 127.4, 126.5, 123.5, 119.3, 118.8, 65.7, 56.5, 47.8, 29.4.

Example 5

Synthesis of cis-5-chloro-2,3,3a,12b-tetrahydro-2-methyl-1H-dibenz[2,3:6,7]oxepino[4,5-c]pyrrol-1-one (compound cis-VIb)

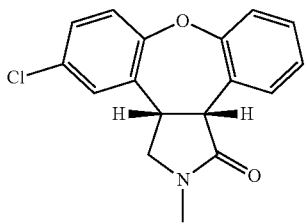 [SMILES: CN1C[C@@H]2c3cc(Cl)ccc3Oc3ccccc3[C@@H]2C1=O]

A mixture of 3 g (9.4 mmol) of 3-[2-(4-chlorophenoxy)phenyl]-4-hydroxy-1-methylpyrrolidine-2-one (compound XIIIb) and 40 g of polyphosphoric acid was stirred overnight at 110° C. After cooling down to room temperature, the resulting mixture was poured into 150 mL of an ice-water mixture. 100 mL of dichloromethane were added, and the organic phase was extracted. The aqueous phase was washed with 50 mL of dichloromethane. The organic phases were combined, washed with brine, and evaporated under vacuum. The crude product was purified by column chromatography to obtain 0.5 g of cis-5-chloro-2,3,3a,12b-tetrahydro-2-methyl-1H-dibenz[2,3:6,7]oxepino[4,5-c]pyrrol-1-one (compound cis-VIb). Yield: 17.7%.

¹H-NMR (400 MHz, DMSO-d₆, 25° C.) δ (ppm): 7.65 (d, 1 H, J=8.8 Hz), 7.57 (dd, 1 H, J=7.6 Hz, J=0.8 Hz), 7.47 (d, 1 H, J=2.8 Hz), 7.41 (dd, 1 H, J=8.6 Hz, J=2.6 Hz), 7.29 (m, 2 H), 7.16 (ddd, 1 H, J=8.4 Hz, J=8.4 Hz, J=1.2 Hz), 4.75 (d, 1 H, J=8.8 Hz), 3.70 (d, 1 H, J=10.0 Hz), 2.96 (m, 1 H), 2.66 (s, 3 H), 1.60 (d, 1 H, J=13.6 Hz). ¹³C-NMR (100.6 MHz, DMSO-d₆, 25° C.) δ (ppm): 174.3, 159.9, 156.8, 136.02, 136.00, 131.2, 130.0, 129.4, 129.3, 128.7, 125.9, 125.7, 123.3, 62.6, 45.5, 36.5, 28.1. MS (electrospray +): 300.1 (100%), 302.1 (50%).

Example 6

Synthesis of methyl 2-(4-chlorophenoxy)phenylacetate (compound VIIIb)

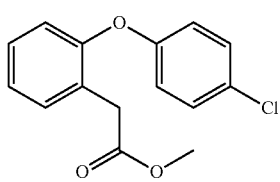 [SMILES: COC(=O)Cc1ccccc1Oc1ccc(Cl)cc1]

70 g (0.27 mol) of 2-(4-chlorophenoxy)phenylacetic acid (compound XVIb), as obtained in Example 1, were dissolved in 600 mL of methanol. The solution was heated to 50-55° C. and stirred at this temperature for 1 hour. Then, 10 g (0.10 mol) of sulfuric acid were added, and the resulting mixture was stirred at 50-55° C. overnight. The solvent was removed by distillation, and the residue was dissolved in 600 mL of ethyl acetate. The solution was washed with 500 mL of an aqueous saturated solution of sodium bicarbonate, dried with anhydrous sodium sulfate and evaporated under reduced pressure, to obtain 45 g of methyl 2-(4-chlorophenoxy)phenylacetate (compound VIIIb) after chromatographic purification. Yield: 61.0%.

Example 7

Synthesis of methyl 2-[2-(4-chlorophenoxy)phenyl]-3-hydroxyacrylate (compound IXb)

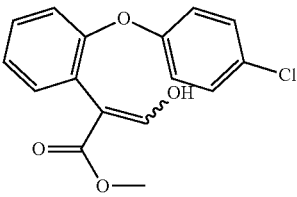 [SMILES: COC(=O)C(=CO)c1ccccc1Oc1ccc(Cl)cc1]

12.92 g (0.32 mol) of a 60% sodium hydride dispersion in mineral oil were suspended in 400 mL of tetrahydrofuran. After cooling to 0-5° C., a solution containing 45 g (0.16 mol) of methyl 2-(4-chlorophenoxy)phenylacetate (compound VIIIb), as obtained in Example 6, in 300 mL of tetrahydrofuran, was added dropwise while keeping the temperature below 10° C. After the addition, the reaction mixture was stirred at 0-5° C. for 30 minutes. Then, 36.3 g (0.60 mol) of methyl formate were added dropwise, while keeping the temperature below 10° C. After the addition, the reaction mixture was stirred at room temperature overnight. 50 mL of 2 M aqueous hydrochloric acid were added. Then, 200 mL of ethyl acetate were added and the phases were decanted. The organic phase was extracted and washed with 200 mL of water and 200 mL of saturated sodium chloride. The organic phase was concentrated to dryness under reduced pressure, to obtain 40 g of methyl 2-[2-(4-chlorophenoxy)phenyl]-3-hydroxyacrylate (compound IXb) after chromatographic purification. Yield: 80.7%.

Example 8

Synthesis of methyl 2-chlorodibenzo[b,f]oxepin-10-carboxylate (compound Xb)

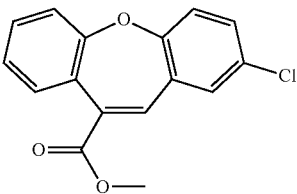 [SMILES: COC(=O)C1=Cc2cc(Cl)ccc2Oc2ccccc21]

40 g (0.13 mol) of methyl 2-[2-(4-chlorophenoxy)phenyl]-3-hydroxyacrylate (compound IXb), as obtained in Example 7, were dissolved in 130 g of pyrophosphoric acid. The solution was stirred at 80° C. for 2 hours. After cooling to room temperature, hexane (250 mL), toluene (500 mL) and water (500 mL) were added to the reaction mixture. The phases were decanted. The organic layer was extracted, washed with 500 mL of saturated aqueous sodium bicarbonate and with 500 mL of saturated sodium chloride, and evaporated under reduced pressure. The resulting oil was crystallized from n-butanol (50 mL) to obtain 16.9 g of methyl 2-chlorodibenzo[b,f]oxepin-10-carboxylate (compound Xb). Yield: 44.9%.

Example 9

Synthesis of methyl 2-chloro-11-nitromethyl-10,11-dihydrodibenzo[b,f]oxepine-10-carboxylate (compound XIb)

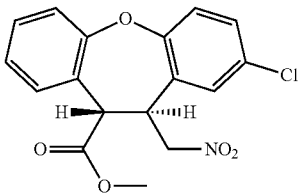 [SMILES: COC(=O)[C@@H]1c2ccccc2Oc2ccc(Cl)cc2[C@H]1C[N+](=O)[O-]]

10 g (35 mmol) of methyl 2-chlorodibenzo[b,f]oxepin-10-carboxylate (compound Xb), as obtained in Example 8, and 2.9 g (17 mmol) of 2-tert-butyl-1,1,3,3-tetramethylguanidine, were dissolved in 120 mL of tetrahydrofuran. The solution was stirred at 30° C. for 30 minutes. Then, 18.7 g (0.31 mol) of nitromethane were added dropwise, while keeping the reaction temperature below 30° C. After the addition, the reaction mixture was stirred at 30° C. overnight. The mixture was adjusted to pH 7 with 1 M aqueous hydrochloric acid and extracted with ethyl acetate. The organic layer was dried with anhydrous sodium sulfate and concentrated under reduced pressure. The resulting oil was crystallized from petroleum ether (50 mL) to obtain 6.6 g of methyl 2-chloro-11-nitronnethyl-10,11-dihydrodibenzo[b,f]oxepine-10-carboxylate (compound XIb). Yield: 54.4%.

Example 10

Synthesis of methyl 11-aminomethyl-2-chloro-10,11-dihydrodibenzo[b,f]oxepine-10-carboxylate (compound XIIb)

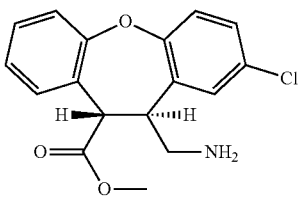

6 g (17 mmol) of methyl 2-chloro-11-nitronnethyl-10,11-dihydrodibenzo[b,f]oxepine-10-carboxylate (compound XIb), as obtained in Example 9, were dissolved in 50 mL of tetrahydrofuran. 1 g of Ni-Raney catalyst was added, and the mixture was stirred under 50 psi (3447 hPa) of hydrogen at 30° C. for 48 hours. The catalyst was removed by filtration, and the resulting solution was concentrated under reduced pressure to obtain 3.7 g of methyl 11-aminomethyl-2-chloro-10,11-dihydrodibenzo[b,f]oxepine-10-carboxylate (compound XIIb). Yield: 67.5%.

Example 11

Synthesis of trans-5-chloro-2,3,3a,12b-tetrahydro-1H-dibenz[2,3:6,7]oxepino[4,5-c]pyrrol-1-one (compound trans-XVIIb)

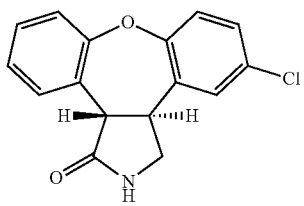 [SMILES: O=C1NC[C@@H]2c3cc(Cl)ccc3Oc3ccccc3[C@@H]12]

2.3 g (7.2 mmol) of methyl 11-aminomethyl-2-chloro-10,11-dihydrodibenzo[b,f]oxepine-10-carboxylate (compound XIIb), as obtained in Example 10, were suspended in a mixture of 20 mL of methanol and 2 mL of 2 M aqueous sodium hydroxide. The mixture was stirred at room temperature overnight. The resulting solid was filtered and washed with methanol, to obtain 1.5 g of trans-5-chloro-2,3,3a,12b-tetrahydro-1H-dibenz[2,3:6,7]oxepino[4,5-c]pyrrol-1-one (compound trans-XVIIb) as an off-white solid. Yield: 72.5%.

Example 12

Synthesis of trans-5-chloro-2,3,3a,12b-tetrahydro-1H-dibenz[2,3:6,7]oxepino[4,5-c]pyrrol-1-one (compound trans-XVIIb)

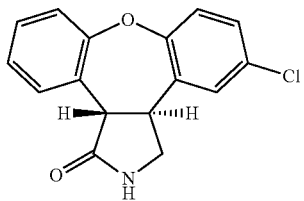 [SMILES: O=C1NC[C@@H]2c3cc(Cl)ccc3Oc3ccccc3[C@@H]12]

180 g (0.52 mol) of methyl 2-chloro-11-nitromethyl-10,11-dihydrodibenzo[b,f]oxepine-10-carboxylate (compound XIb), obtained similarly as described in Example 9, were dissolved in 3 L of tetrahydrofuran. 20 g of Ni-Raney catalyst, previously washed with 500 mL of tetrahydrofuran, were added to the solution, and the mixture was stirred under 50 psi (3447 hPa) of hydrogen at room temperature for 48 hours. The catalyst was removed by filtration and washed with 200 mL of tetrahydrofuran. The filtrate was evaporated to dryness under reduced pressure, and the residue was dissolved in 100 mL of ethyl acetate. The mixture was stirred at 25° C. for 4 days. The resulting suspension was cooled to 0° C. and stirred at this temperature for 1 hour. The solid was removed by filtration and washed with 2×50 mL of cold ethyl acetate, to obtain 63.0 g of trans-5-chloro-2,3,3a,12b-tetrahydro-1H-dibenz[2,3:6,7]oxepino[4,5-c]pyrrol-1-one (compound trans-XVIIb) as a white solid. The filtrate was evaporated to dryness, and the residue was dissolved in 50 mL of ethyl acetate. The mixture was stirred at 25° C. for 2 days. The obtained solid was filtered and dried to obtain a second sample of 22.0 g of trans-5-chloro-2,3,3a,12b-tetrahydro-1H-dibenz[2,3:6,7]oxepino[4,5-c]pyrrol-1-one (compound trans-XVIIb) as a white solid. Yield: 57.5%.

Example 13

Synthesis of 5-chloro-2-phenoxyacetophenone (compound XV)

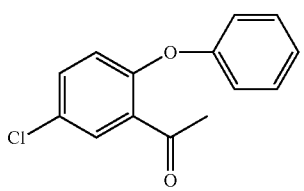 [SMILES: CC(=O)c1cc(Cl)ccc1Oc1ccccc1]

A mixture of 307 g (1.62 mol) 2,5-dichloroacetophenone, 193 g (2.05 mol) of phenol, 302 g (2.19 mol) of potassium carbonate and 15 g (0.24 mol) of copper powder was stirred at 130° C. for 10 hours. The reaction mixture was cooled to room temperature, diluted with 500 mL of methyl tert-butyl ether and filtered. The filtered solid was washed with methyl tert-butyl ether and was discarded. The filtrate was washed twice with 500 mL of 1 M aqueous sodium hydroxide. The organic layer was extracted, dried over anhydrous sodium sulfate and evaporated under reduced pressure. The residue was mixed with 350 mL of methanol and stirred at 10° C. for 30 minutes. The resulting suspension was filtered, and the solid was washed with cold methanol, to obtain 236 g of 5-chloro-2-phenoxyacetophenone (compound XV) as an off-white solid. Yield: 58.9%.

Example 14

Synthesis of 5-chloro-2-phenoxyphenylacetic acid (compound XIVa)

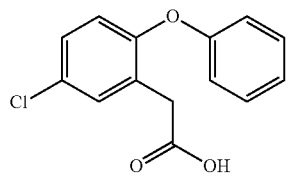 [SMILES: O=C(O)Cc1cc(Cl)ccc1Oc1ccccc1]

A mixture of 200 g (0.81 mol) of 5-chloro-2-phenoxyacetophenone (compound XV), as obtained in Example 13, 112.3 g (1.29 mol) of morpholine and 40 g (1.25 mol) of sulfur was stirred at 110° C. for 12 hours. After cooling to room temperature, 1 L of glacial acetic acid and 1 L of concentrated aqueous hydrochloric acid were added, and the resulting mixture was stirred at reflux temperature for 8 hours. The reaction mixture was concentrated to about ⅓ of its initial volume. Then, 800 mL of water and 800 mL of methyl tert-butyl ether were added. The aqueous layer was separated, washed with 400 mL of methyl tert-butyl ether, and discarded. The organic phases were combined and washed subsequently with 1×500 mL and 2×250 mL of an 8% aqueous solution of sodium carbonate. The aqueous phases were combined, washed with 2×200 mL of methyl tert-butyl ether, and acidified to pH 1 with concentrated hydrochloric acid. 400 mL of petroleum ether were added, and the resulting mixture was stirred at room temperature for 30 minutes. The suspension was filtered, and the solid was dried until constant weight to obtain 143 g of 5-chloro-2-phenoxyphenylacetic acid (compound XIVa). Yield: 67.1%.

Example 15

Synthesis of methyl 5-chloro-2-phenoxyphenylacetate (compound VIIIa)

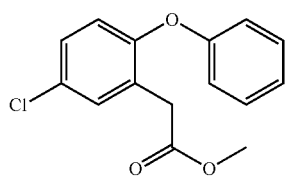 [SMILES: COC(=O)Cc1cc(Cl)ccc1Oc1ccccc1]

233 g (0.89 mol) of 5-chloro-2-phenoxyphenylacetic acid (compound XIVa), as obtained in Example 14, were suspended in 1.2 L of methanol. Then, 60.9 g (0.62 mol) of concentrated sulfuric acid were added dropwise. The mixture was heated to 50° C. and stirred at this temperature for 2 hours. The resulting reaction mixture was concentrated under reduced pressure, and the residue was dissolved in 500 mL of methyl tert-butyl ether. pH was adjusted to 7 by addition of an aqueous saturated solution of sodium carbonate, at a temperature below 25° C. The aqueous layer was extracted and washed with 200 mL of methyl tert-butyl ether. The organic phases were combined, washed with 500 mL of saturated sodium chloride, dried over anhydrous sodium sulfate, and evaporated to dryness under reduced pressure to obtain 240.6 g of methyl 5-chloro-2-phenoxyphenylacetate (compound VIIIa) as an oil. Yield: 98.0%.

Example 16

Synthesis of methyl 2-(5-chloro-2-phenoxyphenyl)-3-hydroxyacrylate (compound IXa)

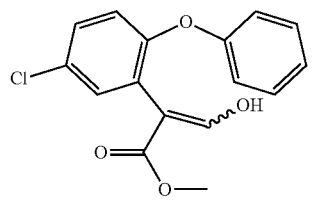 [SMILES: COC(=O)C(=CO)c1cc(Cl)ccc1Oc1ccccc1]

A solution of 200 g (0.72 mol) of methyl 5-chloro-2-phenoxyphenylacetate (compound VIIIa), as obtained in Example 15, and 195.31 g (3.25 mol) of methyl formate in 1.2 L of methyl tert-butyl ether was cooled to 5° C. 118.08 g (1.23 mol) of sodium tert-butoxide were added portionwise, keeping the reaction temperature below 10° C. After the addition, the reaction mixture was stirred at room temperature for 2 hours. pH was adjusted to 7 with 4 M aqueous hydrochloric acid, keeping the reaction temperature below 25° C. The aqueous layer was extracted and washed with 300 mL of methyl tert-butyl ether. The organic phases were combined, washed with 600 mL of saturated sodium chloride, dried over anhydrous sodium sulfate, and evaporated to dryness under reduced pressure to obtain methyl 2-(5-chloro-2-phenoxyphenyl)-3-hydroxyacrylate (compound IXa) as an oil, which was used in the next step (see Example 17) without further purification.

Example 17

Synthesis of methyl 2-chlorodibenzo[b,f]oxepin-1'-carboxylate (compound Xa)

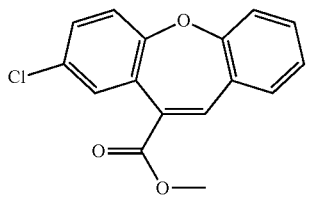 [SMILES: COC(=O)C1=Cc2ccccc2Oc2ccc(Cl)cc21]

A mixture of 415.23 g (2.33 mol) of pyrophosphoric acid and 22.14 g of water at 0° C. was added over methyl 2-(5-chloro-2-phenoxyphenyl)-3-hydroxyacrylate (compound IXa) as obtained in Example 16. The reaction mixture was stirred at 60° C. for 2 hours. After cooling to 20° C., 500 mL of water and 1.4 L of methyl tert-butyl ether were added. The aqueous layer was extracted and washed with 200 mL of methyl tert-butyl ether. The organic phases were combined, washed with 400 mL of an aqueous saturated solution of sodium bicarbonate and 400 mL of saturated sodium chloride, dried over anhydrous sodium sulfate and concentrated to dryness under reduced pressure. The residue was suspended in 400 mL of n-butanol and stirred at room temperature for 1 hour, and at 0° C. for 2 hours. The resulting suspension was filtered, and the solid was dried until constant weight to obtain 161 g of methyl 2-chlorodibenzo[b,f]oxepin-11-carboxylate (compound Xa) as an off-white solid. Yield: 77.7%.

Example 18

Synthesis of methyl 2-chloro-10-nitromethyl-10,11-dihydrodibenzo[b,f]oxepine-1'-carboxylate (compound XIa)

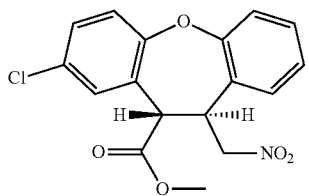

161 g (0.56 mol) of methyl 2-chlorodibenzo[b,f]oxepin-11-carboxylate (compound Xa), as obtained in Example 17, were suspended in 342 g (5.60 mol) of nitromethane. Then, 34.19 g (0.22 mol) of 1,8-diazabicyclo[5.4.0]undec-7-ene (DBU) were added portionwise while keeping the reaction temperature below 35° C. After the addition, the reaction mixture was stirred at room temperature overnight. Then, 800 mL of methyl tert-butyl ether, 250 mL of 1 M aqueous hydrochloric acid and 250 mL of water were added over the reaction, and the resulting mixture was stirred at room temperature for 30 minutes. The aqueous layer was extracted and washed with 200 mL of methyl tert-butyl ether. The organic phases were combined, washed with 550 mL of saturated sodium chloride, dried over anhydrous sodium sulfate and evaporated to dryness. The residue was suspended in 240 mL of n-butanol and stirred at room temperature for 1 hour. The resulting suspension was filtered, and the solid was dried until constant weight to obtain 150 g of methyl 2-chloro-10-nitronnethyl-10,11-dihydrodibenzo[b,f]oxepine-11-carboxylate (compound XIa) as an off-white solid. Yield: 76.8%.

Example 19

Synthesis of methyl 10-aminomethyl-2-chloro-10,11-dihydrodibenzo[b,f]oxepine-1'-carboxylate (compound XIIa)

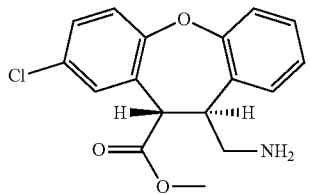 [SMILES: COC(=O)[C@@H]1c2cc(Cl)ccc2Oc2ccccc2[C@H]1C[N+](=O)[O-]]

An aqueous slurry of Ni-Raney (containing 30 g of Ni on a dry basis) was washed with tetrahydrofuran, and added over a solution of 270 g (0.78 mol) of methyl 2-chloro-10-nitromethyl-10,11-dihydrodibenzo[b,f]oxepine-11-carboxylate (compound XIa), as obtained in Example 18, in 2.7 L of tetrahydrofuran. The suspension was stirred under 50-60 psi (3447-4136 hPa) of hydrogen at room temperature for 2 days. The catalyst was removed by filtration, and the resulting solution was concentrated under reduced pressure to obtain methyl 10-aminomethyl-2-chloro-10,11-dihydrodibenzo[b,f]oxepine-11-carboxylate (compound XIIa), which was used in the next step (see Example 20) without further purification.

Example 20

Synthesis of trans-1'-chloro-2,3,3a,12b-tetrahydro-1H-dibenz[2,3:6,7]oxepino[4,5-c]pyrrol-1-one (compound trans-XVIIa)

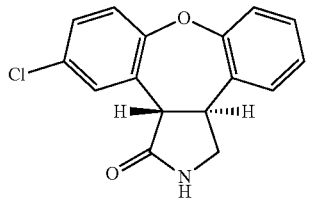 [SMILES: O=C1NC[C@@H]2c3ccccc3Oc3ccc(Cl)cc3[C@@H]12]

The methyl 10-aminomethyl-2-chloro-10,11-dihydrodibenzo[b,f]oxepine-11-carboxylate (compound XIIa) obtained in Example 19 was mixed with 150 mL of ethyl acetate and stirred at room temperature for 4 days. The resulting suspension was filtered, and the solid was washed with ethyl acetate. The resulting solid was further purified by means of successive digestion steps in methanol (50 mL per g

33 of crude product), until an appropriate purity was achieved. After 7 digestion steps, 60 g of trans-1'-chloro-2,3,3a,12b-tetrahydro-1H-dibenz[2,3:6,7]oxepino[4,5-c]pyrrol-1-one (compound trans-XVIIa) were obtained as a white powder. Yield: 27.0%. Purity (HPLC, method 1): 98.5%.

Example 21

Synthesis of trans-1'-chloro-2,3,3a,12b-tetrahydro-1H-dibenz[2,3:6,7]oxepino[4,5-c]pyrrol-1-one (compound trans-XVIIa)

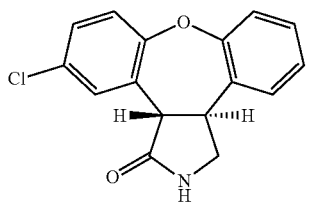 [SMILES: O=C1NC[C@@H]2c3ccccc3Oc3ccc(Cl)cc3[C@@H]12]

An aqueous slurry of Ni-Raney (containing 40 g of Ni on a dry basis) was washed with tetrahydrofuran, and added over a solution of 400 g (1.15 mol) of methyl 2-chloro-10-nitromethyl-10,11-dihydrodibenzo[b,f]oxepine-11-carboxylate (compound XIa), obtained similarly as described in Example 18, in 2.5 L of tetrahydrofuran. The suspension was stirred under 50-60 psi (3447-4136 hPa) of hydrogen at room temperature for 2 days. The catalyst was removed by filtration, and the resulting solution was concentrated under reduced pressure. The residue was mixed with 300 mL of ethyl acetate, and the solvent was removed by distillation under reduced pressure. This step was repeated. The resulting residue was mixed with 300 mL of ethyl acetate and stirred at 25° C. for 4 days. The resulting suspension was filtered, and the solid was washed with ethyl acetate. The resulting solid was further purified by means of three successive digestion steps in methanol (5 mL per g of crude product), to obtain 222 g of trans-1'-chloro-2,3,3a,12b-tetrahydro-1H-dibenz[2,3:6,7]oxepino[4,5-c]pyrrol-1-one (compound trans-XVIIa). Yield: 67.6%.

Example 22

Synthesis of trans-5-chloro-2,3,3a,12b-tetrahydro-1H-dibenzo[2,3:6,7]oxepino[4,5-c]pyrrole hydrochloride (compound trans-XVIII hydrochloride)

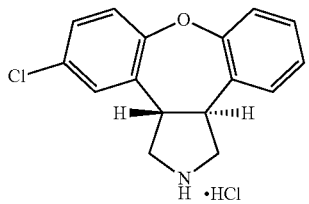 [SMILES: Clc1ccc2c(c1)[C@H]1CNC[C@@H]1c1ccccc1O2 ; Cl]

A mixture of 95.0 g (0.33 mol) of trans-1'-chloro-2,3,3a,12b-tetrahydro-1H-dibenz[2,3:6,7]oxepino[4,5-c]pyrrol-1-one (compound trans-XVIIa), as obtained in Example 20, 193.3 g (1.66 mol) of triethylsilane and 236.0 g (1.66 mol) of boron trifluoride diethyl etherate was heated to 105° C. and stirred at this temperature for 24 hours. The resulting suspension was cooled down to 0° C., and 50 mL of water were added dropwise. pH was adjusted to above 10 by dropwise addition of a 20% aqueous sodium hydroxide solution. The mixture was extracted with 2×1 L of dichloromethane at 30° C. The organic phases were combined, washed with 500 mL of water and dried over anhydrous sodium sulphate. The solution was concentrated to about 200 mL. Then, a mixture of 33 mL of a 10M solution of hydrogen chloride in ethanol, and 50 mL of dichloromethane, was added dropwise over the concentrated solution. The solvents were removed under reduced pressure. 250 mL of ethanol were added and subsequently removed under reduced pressure. Finally, the resulting solid was suspended in 500 mL of ethyl acetate. The suspension was filtered, and the solid was washed with 50 mL of ethyl acetate and dried until constant weight to obtain 66.0 g of trans-5-chloro-2,3,3a,12b-tetrahydro-1H-dibenzo[2,3:6,7]oxepino[4,5-c]pyrrole hydrochloride (compound trans-XVIII hydrochloride) as a white solid. Yield: 64.4%.

Example 23

Synthesis of trans-5-chloro-2,3,3a,12b-tetrahydro-1H-dibenzo[2,3:6,7]oxepino[4,5-c]pyrrole hydrochloride (compound trans-XVIII hydrochloride)

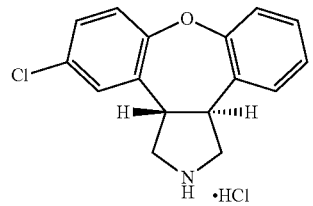 [SMILES: Clc1ccc2c(c1)[C@H]1CNC[C@@H]1c1ccccc1O2 ; Cl]

0.526 g (1.84 mmol) of trans-11-chloro-2,3,3a,12b-tetrahydro-1H-dibenz[2,3:6,7]oxepino[4,5-c]pyrrol-1-one (compound trans-XVIIa) and 17.5 mL of toluene were charged to a 50 mL round-bottomed flask equipped with a Dean-Stark distillation setup. The mixture was heated to reflux and stirred for about 10 min before it was cooled to 0° C. Then trifluoromethanesulfonic anhydride (0.32 mL, 1.9 mmol) was added dropwise and the mixture stirred for about 30 minutes. Sodium borohydride (100 mg, 2.6 mmol) was then added followed by anhydrous tetrahydrofuran (8.6 mL). The obtained solution was allowed to heat to room temperature and stirred over about 20 h. Water (8.6 mL) and 1M hydrochloric acid (0.1 mL) were added, and the mixture heated to reflux, stirred for 2 h and allowed to cool down to room temperature. 6 mL of saturated sodium carbonate solution were added, and the obtained layers were separated. The aqueous layer was extracted with diethyl ether (26 mL) three times, and the obtained organic layers were dried with sodium sulfate, filtered, rotary evaporated and dried in the vacuum oven to yield 0.797 g of a crude oil.

510 mg of the obtained crude and 10 mL of 1.25 M hydrogen chloride in ethanol were heated to reflux and stirred for 2 h. Then the mixture was rotary evaporated and 10 mL of ethyl acetate was added to the obtained residue. A suspension formed, which was stirred for 27 min. The solid was filtered and washed with ethyl acetate (2×1 mL), then it was dried under vacuum to yield 152 mg. Yield: 43%. Purity (HPLC, method 2): 97.4%.

Example 24

Synthesis of trans-5-chloro-2,3,3a,12b-tetrahydro-1H-dibenzo[2,3:6,7]oxepino[4,5-c]pyrrole (compound trans-XVIII)

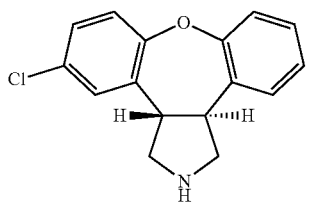 [SMILES: Clc1ccc2c(c1)[C@H]1CNC[C@@H]1c1ccccc1O2]

1.164 g (8.7 mmol) of aluminium chloride were dissolved in tetrahydrofuran (15 mL) at 10° C. The solution was then cooled to 3° C. and a 2 M lithium aluminum hydride solution in tetrahydrofuran (7.4 mL, 14.8 mmol) was added over about 13 min. The addition funnel was washed with tetrahydrofuran (2 mL) at the end of the addition. After about 10 min at 0° C., a solution of 1.52 g (5.2 mmol) of trans-1'-chloro-2,3,3a,12b-tetrahydro-1H-dibenz[2,3:6,7]oxepino[4,5-c]pyrrol-1-one (compound trans-XVIIa) in 25 mL of tetrahydrofuran was added dropwise. The obtained solution was stirred for 3 h before it was allowed to heat up to room temperature and left stirring overnight. The reaction mixture was cooled to 2° C. and 16.5 mL of a 0.6 M sodium hydroxide solution were cautiously added over about 20 min. Then the mixture was allowed to warm to room temperature and toluene (22.5 mL) and water (15 mL) were added. The mixture was filtered through diatomaceous earth and the filter was washed with toluene (10 mL), twice. The combined liquors were decanted and the aqueous layer was extracted with toluene (15 mL), twice. The combined organic layers were washed with a saturated solution of sodium chloride (45 mL), twice, and the obtained organic layer was dried with anhydrous sodium sulfate, filtered and rotary evaporated. After drying under vacuum, the obtained oil weighed 1.36 g.

Example 25

Synthesis of trans-5-chloro-2,3,3a,12b-tetrahydro-1H-dibenzo[2,3:6,7]oxepino[4,5-c]pyrrole (compound trans-XVIII)

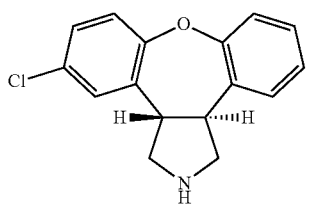 [SMILES: Clc1ccc2c(c1)[C@H]1CNC[C@@H]1c1ccccc1O2]

1.55 g (5.4 mmol) of trans-11-chloro-2,3,3a,12b-tetrahydro-1H-dibenz[2,3:6,7]oxepino[4,5-c]pyrrol-1-one (compound trans-XVIIa) was dissolved in 32.5 mL of anhydrous tetrahydrofuran. 2.1 mL of N,N-diethylaniline-borane complex (11.5 mmol) were added dropwise and the obtained solution was stirred at room temperature for 30 min before heating to reflux. The reaction mixture was stirred for 8 h then it was allowed to cool to room temperature overnight. The mixture was reheated to reflux and stirred for 5 h before allowing to cool down to room temperature. 3 mL of a 6 M hydrochloric acid were added and the mixture refluxed for 1 h and overnight at room temperature. The mixture was then basified with 95 mL of 0.25 M potassium hydroxide and extracted with diethyl ether (50 mL), three times. The organic layers were combined and dried with anhydrous sodium sulfate, filtered and rotary evaporated.

Example 26

Synthesis of trans-5-chloro-2,3,3a,12b-tetrahydro-1H-dibenzo[2,3:6,7]oxepino[4,5-c]pyrrole (compound trans-XVIII)

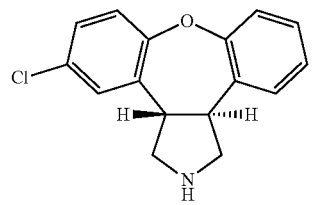 [SMILES: Clc1ccc2c(c1)[C@H]1CNC[C@@H]1c1ccccc1O2]

0.53 g (1.9 mmol) of trans-11-chloro-2,3,3a,12b-tetrahydro-1H-dibenz[2,3:6,7]oxepino[4,5-c]pyrrol-1-one (compound trans-XVIIa) was suspended in 5 mL of anhydrous tetrahydrofuran and cooled to -2° C. 8.8 mL of borane-tetrahydrofuran complex (8.7 mmol) were added dropwise and the obtained solution was allowed to warm up to room temperature. The reaction mixture was stirred for 20.5 h and 5 mL of anhydrous tetrahydrofuran were added. After further 25 h at room temperature, 8.8 mL of borane-tetrahydrofuran complex (8.7 mmol) were added and the mixture stirred for 4 h before adding 1.25 M hydrogen chloride in ethanol (25.2 mL, 31.5 mmol). After 3 days the reaction mixture was rotary evaporated and toluene (25 mL) and 1 M sodium hydroxide (10.5 mL) were added to the residue. More toluene (25 mL) and water (10 mL) were added and the mixture vigorously stirred for about 2.5 h. Then the layers were separated and the aqueous layer was extracted with toluene (25 mL), twice. The organic layers were combined and washed with 0.1 M sodium hydroxide (4 mL), dried with anhydrous sodium sulfate, filtered and rotary evaporated.

Example 27

Synthesis of Asenapine Maleate (Compound Trans-I Maleate)

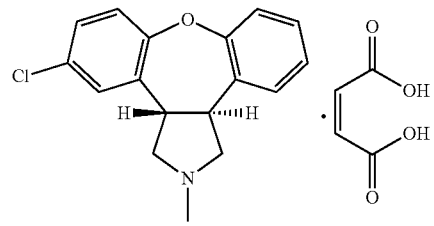

66.0 g (0.21 mol) of trans-5-chloro-2,3,3a,12b-tetrahydro-1H-dibenzo[2,3:6,7]oxepino[4,5-c]pyrrole hydrochloride (compound trans-XVIII hydrochloride), as obtained in Example 22, were suspended in 500 mL of dichloromethane. 1 M aqueous sodium hydroxide was added until the pH was adjusted to above 10. The aqueous phase was extracted and washed with 500 mL of dichloromethane. The combined organic phases were evaporated to dryness to obtain trans-5-chloro-2,3,3a,12b-tetrahydro-1H-dibenzo[2,3:6,7]oxepino[4,5-c]pyrrole (compound trans-XIX) as a free base, which was dissolved in a mixture of 34.81 g (0.43 mol) of a 37% aqueous solution of formaldehyde, 33.94 g (0.65 mol) of 88° A formic acid, and 500 mL of toluene. The resulting mixture was heated to 60° C. and stirred at this temperature for 2 hours. After cooling to room temperature, pH was adjusted to 10 by addition of 1 M aqueous sodium hydroxide. The aqueous layer was extracted and washed with 500 mL of toluene. The organic phases were combined, washed with 500 mL of saturated sodium chloride, dried over anhydrous sodium sulfate and evaporated to dryness under reduced pressure to give asenapine (free base) as an oil, which was subsequently dissolved in 500 mL of isopropanol at 50° C. Then, 27.23 g (0.23 mol) of maleic acid and 5.0 g of active charcoal were added, and the resulting mixture was stirred at 65° C. for 1 hour. The suspension was filtered, and the solid was washed with 50 mL of hot isopropanol. The filtrate was cooled slowly to 10° C., and seeded with asenapine maleate at this temperature. After stirring for 2 hours at 10° C., the resulting suspension was filtered, and the solid was washed with 50 mL of cold isopropanol. The solid was recrystallized from 500 mL of isopropanol and dried at 70° C. under reduced pressure, until constant weight, to obtain 45.0 g of asenapine maleate (compound trans-I maleate) as a white powder. Yield: 52.3%. Purity (HPLC, method 1): 99.8%. Assay (titration with NaOH): 100.2%.

The invention claimed is:

1. A process for the preparation of compound trans-(I),

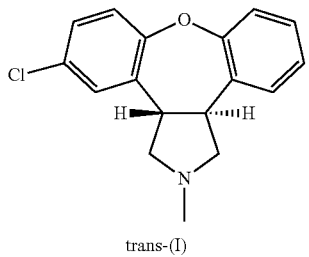 [SMILES: CN1C[C@@H]2c3ccccc3Oc3ccc(Cl)cc3[C@H]2C1]

trans-(I)

or a salt thereof, the process comprising:

(a) reducing desmethyl-lactam (XVII) in the presence of at least one reducing agent, optionally in the presence of one or more Lewis acids

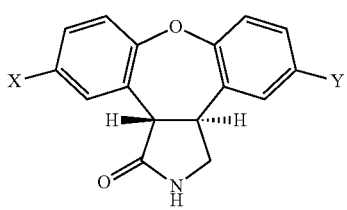

(XVII)

to give desmethylasenapine (XVIII),

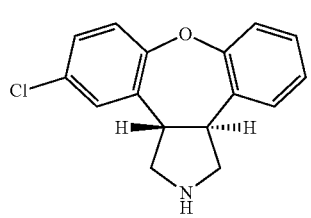

(XVIII)

(b) methylating desmethylasenapine (XVIII) in the presence of a methylating agent to give compound trans-(I); and (c) optionally converting compound trans-(I) to a salt thereof, wherein X is H and Y is Cl or wherein X is Cl and Y is H.

2. The process according to claim 1 further comprising the ring-closing of the amino-ester (XII') or the amino-acid (XVI),

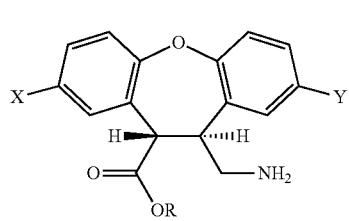

(XII')

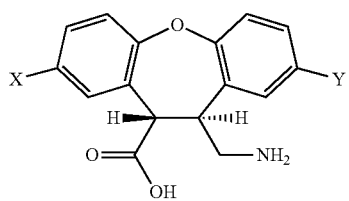

(XVI)

to prepare the desmethyl-lactam (XVII),

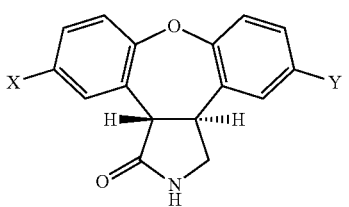

(XVII)

wherein the ring-closing is carried out in the presence of any acidic catalyst or any mild basic catalyst, wherein X is H and Y is Cl or wherein X is Cl and Y is H and R is any alkyl, optionally substituted; benzyl, optionally substituted or phenyl, optionally substituted.

3. The process according to claim 2, wherein the ring-closing of the amino-ester (XII') is catalyzed by the unreacted amino-ester (XII').

4. The process according to claim 2, wherein the mild basic catalyst is sodium or potassium hydroxide.

5. The process according to claim 2 further comprising:
(a) reducing the nitro-ester (XI'),

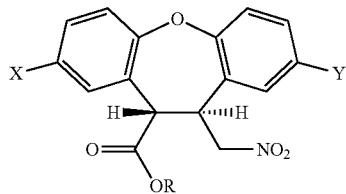
(XI')

to give the amino-ester (XII'),

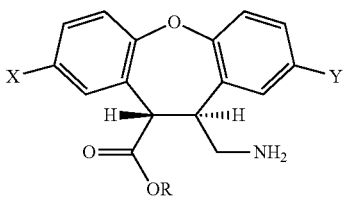
(XII')

(b) optionally hydrolyzing the amino-ester (XII') into the amino-acid (XVI),

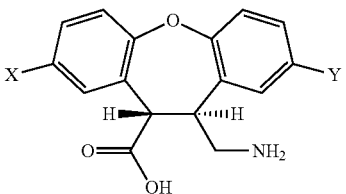
(XVI)

wherein X is H and Y is Cl or wherein X is Cl and Y is H and R is any alkyl, optionally substituted; benzyl, optionally substituted or phenyl, optionally substituted.

6. The process according to claim 1, wherein desmethyl-lactam (XVII) is

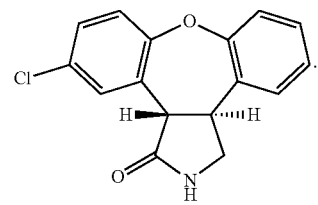
(XVIIa)

7. The process according to claim 1, wherein the at least one reducing agent comprises silane or $^{i}Bu_2AlH$.

8. The process according to claim 7, wherein the silane is triethylsilane.

9. The process according to claim 1, wherein the one or more Lewis acids comprises boron trifluoride diethyl etherate.

10. The process according to claim 1, wherein the methylating agent comprises a mixture of formaldehyde and formic acid.

11. The process according to claim 1, wherein the reduction of the desmethyl-lactam (XVII) is carried out in the presence of triethylsilane and boron trifluoride diethyl etherate; and wherein the desmethylasenapine (XVIII) is methylated to give compound trans-(I) in the presence of a mixture of formaldehyde and formic acid.

12. The process according to claim 1, wherein the reduction of the desmethyl-lactam (XVII) is carried out in the presence of $^{i}Bu_2AlH$; and wherein the desmethylasenapine (XVIII) is methylated to give compound trans-(I) in the presence of a mixture of formaldehyde and formic acid.

13. The process according to claim 6 further comprising the ring-closing of the amino-ester (XIIa)

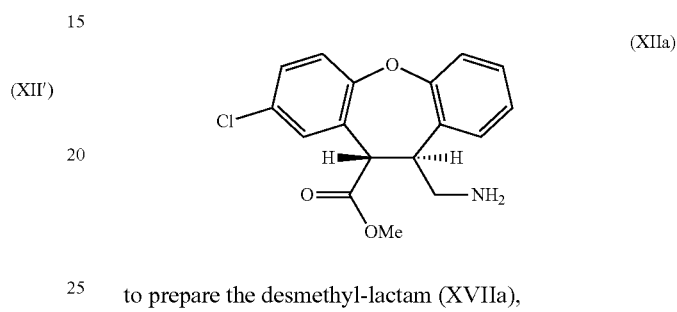
(XIIa)

to prepare the desmethyl-lactam (XVIIa),

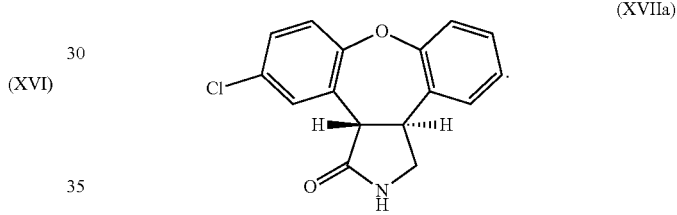
(XVIIa)

wherein the ring-closing of the amino-ester (XIIa) is catalyzed by the unreacted amino-ester (XIIa).

14. The process according to claim 13 further comprising:
(a) reducing the nitro-ester (XIa),

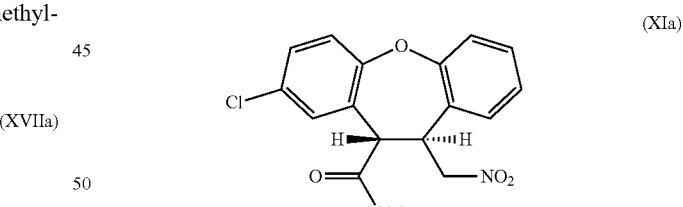
(XIa)

to give the amino-ester (XIIa),

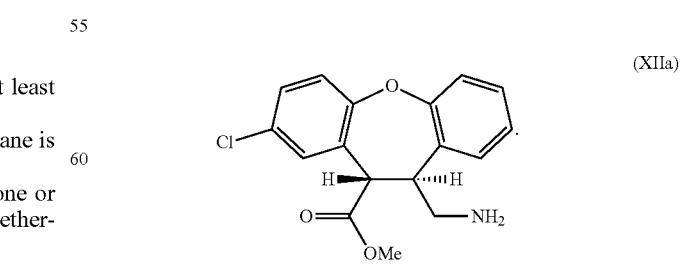
(XIIa)

* * * * *